US005700470A

United States Patent [19]
Saito et al.

[11] Patent Number: 5,700,470
[45] Date of Patent: Dec. 23, 1997

[54] RECOMBINANT ADENOVIRUS WITH REMOVED EZA GENE AND METHOD OF PREPARATION

[75] Inventors: Izumu Saito; Yumi Kanegae, both of Tokyo; Michio Nakai, Osaka, all of Japan

[73] Assignee: Sumitomo Pharmaceuticals Company, Limited, Osaka, Japan

[21] Appl. No.: 615,048

[22] Filed: Mar. 12, 1996

[30] Foreign Application Priority Data

Mar. 15, 1995 [JP] Japan .................................. 7-084891
Sep. 29, 1995 [JP] Japan .................................. 7-276335

[51] Int. Cl.⁶ .......................... A61K 39/23; A61K 39/12; C12N 15/00; C12N 1/20
[52] U.S. Cl. .................................. 424/233.1; 424/199.1; 435/320.1; 435/252.32; 514/44; 536/23.72; 935/22; 935/23; 935/52
[58] Field of Search ........................ 435/320.1, 252.32; 514/44; 536/23.72; 424/199.1, 233.1; 936/22, 23, 52

[56] References Cited

FOREIGN PATENT DOCUMENTS

| 0220009 | 4/1987 | European Pat. Off. . |
| 0300422 | 1/1989 | European Pat. Off. . |
| WO 9428152 | 12/1994 | WIPO . |
| WO 9428938 | 12/1994 | WIPO . |
| WO 9502697 | 1/1995 | WIPO . |
| WO 9527071 | 10/1995 | WIPO . |
| WO 9534671 | 12/1995 | WIPO . |

OTHER PUBLICATIONS

Sauer, B. et al, 1988, PNAS, vol. 85, pp. 5166–5170.
Niwa et al., "Efficient Selection for High-Expression Transfectants with a Novel Eukaryotic Vector," *Gene*, 108, pp. 193–200 (1991).
Engelhardt et al., "Direct Gene Transfer of Human CFTR Into Human Bronchial Epithelia of Xenografts with El-Deleted Adenoviruses," *Nature Genetics*, vol. 4, pp. 27–34 (May 1993).
Saito et al., "Adenovirus Vector," the 41st General Meeting: The Society of Japanese Virologists (1993).

Kanegae et al., "Adenovirus Vector and Gene Therapy," *Experimental Medicine*, vol. 12, No. 3 (1994).
Kanegae et al., Experimental Medicine Supplemental Volume, Biomanual Series 4, pp. 43–58 (1994).
Gu et al., "Deletion of DNA Polymerase . . . Targeting," *Science*, vol. 265, Jul. 1, 1994, pp. 103–106.
Anton et al., "Site Specific Recombinaiton Mediated . . . Expression," *Journal of Virology*, Aug. 1995, pp. 4600–4606.
*First Annual Meeting 1995 Japanese Society of Gene Therapy*, Program and Abstract, May 21, 1995, Kanagae et al, "Application of Cre/LoxP System to Adenovirus Vector".
Kanegae et al., "Efficient Gene Activation . . . Recombinase," *Nucleic Acids Research*, vol. 23, No. 19, pp. 3816–3821 (1995).
Bergemann et al., "Excision of Specific DNA . . . Recombination, " *Nucleic Acids Research*, vol. 23, No. 21, pp. 4451–4456 (1995).
The 43rd Annual Meeting of the Society of Japanese Virologists, (Sep. 29, 1995), 2016, p. 126.
*The Second Brain Tumor Gene Therapy Meeting*, Feb. 3 and 4, 1995, "Adenovirus Vector".
Engelhardt et al, "Ablation of E2A in recombinant adenoviruses improvesd transgene persistence . . . ," *Proc. Natl. Acad. Sci.*, vol. 91, pp. 6196–6200, Jun. 1994.
Yang et al, "Inactivation of E2A in recombinant adenoviruses improves the prospects for gene therapy in cystic fibrosis," *Nature Genetics*, vol. 7, pp. 362–369, Jul. 1994.
Gorziglia et al, "Elimination of both E1 and E2a from Adenovirus Vectors Further Improves Prospects for In Vivo Human Gene Therapy," *J. Virology*, vol. 70, No. 6, pp. 4173–4178, Jun. 1996.

*Primary Examiner*—Marian C. Knode
*Assistant Examiner*—Ali R. Salimi
*Attorney, Agent, or Firm*—Sughrue, Mion, Zinn, Macpeak & Seas, PLLC

[57] ABSTRACT

A recombinant DNA virus for transfecting an animal cell and bearing a foreign gene and a promoter capable of regulating expression of the foreign gene is completely deleted of the function of E2A gene. The recombinant DNA virus can thus stably transduce the foreign gene into various animal cells, which leads to continuous expression of the foreign gene in the animal cells. The continuous expression of the foreign gene can provide an effective treatment of hereditary disease.

31 Claims, 4 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

ATAACTTCGT ATAGCATACA TTATACGAAG TTAT    3 4

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: other nucleic acid
       ( A ) DESCRIPTION: /desc ="synthetic linker"

( x i ) SEQUENCE DESCRIPTION: SEQ ID NO:2:

CGATTTAAAT CGATTGTCGA CTCGCGA                                                    27

( 2 ) INFORMATION FOR SEQ ID NO:3:

( i ) SEQUENCE CHARACTERISTICS:
       ( A ) LENGTH: 36 base pairs
       ( B ) TYPE: nucleic acid
       ( C ) STRANDEDNESS: double
       ( D ) TOPOLOGY: linear ( i i ) MOLECULE TYPE: other nucleic acid
       ( A ) DESCRIPTION: /desc ="synthetic DNA"

( x i ) SEQUENCE DESCRIPTION: SEQ ID NO:3:

ATCGATTCTA GACTAGTTTA ATTAATTTAA ATCGAT                                          36

( 2 ) INFORMATION FOR SEQ ID NO:4:

( i ) SEQUENCE CHARACTERISTICS:
       ( A ) LENGTH: 52 base pairs
       ( B ) TYPE: nucleic acid
       ( C ) STRANDEDNESS: double
       ( D ) TOPOLOGY: linear ( i i ) MOLECULE TYPE: other nucleic acid
       ( A ) DESCRIPTION: /desc ="synthetic DNA"

( x i ) SEQUENCE DESCRIPTION: SEQ ID NO:4:

CGAACGCGTA TAACTTCGTA TAGCATACAT TATACGAAGT TATCTCGAGT CG                        52

( 2 ) INFORMATION FOR SEQ ID NO:5:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc ="oligonucleotide"

( x i ) SEQUENCE DESCRIPTION: SEQ ID NO:5:

CAACTCCATG CTCAACAGTC CCCAGGTACA                                                 30

( 2 ) INFORMATION FOR SEQ ID NO:6:

( i ) SEQUENCE CHARACTERISTICS:
       ( A ) LENGTH: 26 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc ="oligonucleotide"

( x i ) SEQUENCE DESCRIPTION: SEQ ID NO:6:

GATTTTAAA CGGCGCAGAC GGCAAG                                                      26

( 2 ) INFORMATION FOR SEQ ID NO:7:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear (  i i  ) MOLECULE TYPE: other nucleic acid
          ( A ) DESCRIPTION: /desc ="oligonucleotide"

(  x i  ) SEQUENCE DESCRIPTION: SEQ ID NO:7:

GTGAGCTTAG AAAACCCTTA G                                                        2 1

( 2 ) INFORMATION FOR SEQ ID NO:8:

(  i  ) SEQUENCE CHARACTERISTICS:
          ( A ) LENGTH: 31 base pairs
          ( B ) TYPE: nucleic acid
          ( C ) STRANDEDNESS: single
          ( D ) TOPOLOGY: linear (  i i  ) MOLECULE TYPE: other nucleic acid
          ( A ) DESCRIPTION: /desc ="oligonucleotide"

(  x i  ) SEQUENCE DESCRIPTION: SEQ ID NO:8:

AGATACCCCT TTTGCACTGG TGCAAGTTAA C                                             3 1

( 2 ) INFORMATION FOR SEQ ID NO:9:

(  i  ) SEQUENCE CHARACTERISTICS:
          ( A ) LENGTH: 53 base pairs
          ( B ) TYPE: nucleic acid
          ( C ) STRANDEDNESS: single
          ( D ) TOPOLOGY: linear (  i i  ) MOLECULE TYPE: other nucleic acid
          ( A ) DESCRIPTION: /desc ="primer"

(  x i  ) SEQUENCE DESCRIPTION: SEQ ID NO:9:

CGTCTGCAGT GCATCATGAG TAATTTACTG ACCGTACACC AAAATTTGCC TGC                     5 3

( 2 ) INFORMATION FOR SEQ ID NO:10:

(  i  ) SEQUENCE CHARACTERISTICS:
          ( A ) LENGTH: 38 base pairs
          ( B ) TYPE: nucleic acid
          ( C ) STRANDEDNESS: single
          ( D ) TOPOLOGY: linear (  i i  ) MOLECULE TYPE: other nucleic acid
          ( A ) DESCRIPTION: /desc ="primer"

(  x i  ) SEQUENCE DESCRIPTION: SEQ ID NO:10:

GGCTCTAGAG CGCTTAATGG CTAATCGCCA TCTTCCAG                                      3 8

( 2 ) INFORMATION FOR SEQ ID NO:11:

(  i  ) SEQUENCE CHARACTERISTICS:
          ( A ) LENGTH: 119 base pairs
          ( B ) TYPE: nucleic acid
          ( C ) STRANDEDNESS: double
          ( D ) TOPOLOGY: linear (  i i  ) MOLECULE TYPE: other nucleic acid
          ( A ) DESCRIPTION: /desc ="linker DNA"

(  x i  ) SEQUENCE DESCRIPTION: SEQ ID NO:11:

CATGTAATTT AAATCTCGAG ATAACTTCGT ATAATGTATG CTATACGAAG TTATACGCGT              6 0

ATTTAAATGT AAAATAATG TACTAGAGAC ACTTTCAATA AAGGCAAATG CTTTTATTT              1 1 9

( 2 ) INFORMATION FOR SEQ ID NO:12:

(  i  ) SEQUENCE CHARACTERISTICS:
          ( A ) LENGTH: 115 base pairs
          ( B ) TYPE: nucleic acid ( C ) STRANDEDNESS: double
( D ) TOPOLOGY: linear ( i i ) MOLECULE TYPE: other nucleic acid
( A ) DESCRIPTION: /desc ="linker DNA"

( x i ) SEQUENCE DESCRIPTION: SEQ ID NO:12:

```
GTACACTCTC GGGTGATTAT TTACCCCCAC CCTTGCCGTC TGCGCCGATT TAAATCTCGA      60
GATAACTTCG TATAATGTAT GCTATACGAA GTTATACGCG TATTTAAATC CGTTT          115
```

RECOMBINANT ADENOVIRUS WITH REMOVED EZA GENE AND METHOD OF PREPARATION

BACKGROUND OF THE INVENTION

1. Field of the Invention

The present invention relates to a recombinant DNA virus for transfecting an animal cell and to a method for preparation thereof. The present invention further relates to a recombinant DNA viral vector bearing a DNA sequence coding for a recombinase-recognizing sequence, for use in the preparation of the recombinant DNA virus.

2. Related Art Statement

Retrovirus has been often employed as a viral vector for gene transduction. However, retrovirus is transfected only into mitotic cells and integrated into a chromosome of host cells and therefore, retrovirus as a viral vector encounters a problem from a viewpoint of safety, especially in gene therapy. It is thus considered that retrovirus should be limitedly used as a viral vector.

An adenoviral vector is advantageous in that it shows a transducing efficiency of almost 100% in a variety of animal cultured cells, has no positive mechanism for integration into chromosome unlike retrovirus, and can transduce a gene even into a resting cell. In view of such advantages, an adenoviral vector is considered as being applicable over an extremely wide fields for attempting to transduce a foreign gene. It would thus be established in the near future that an adenoviral vector is used as one of major technology for gene therapy.

An adenovirus vector has been widely utilized as one technology for gene therapy or for researching an expression in highly differentiated cells such as a nervous system cell. For a technique of gene therapy, an in vivo gene therapy has been extensively studied wherein a gene which is defective in a living cell is transduced into the cell by direct injection of the gene into a tissue in which the cell exists and functions. In the United States, five research groups have been already allowed to conduct a clinical trial for treating patients with cystic fibrosis by the in vivo gene therapy. Furthermore, researches with gene therapy have also been extended to muscular dystrophy, familial hypercholesterolemia and brain tumor. On the other hand, an adenoviral vector enables transduction of a gene even into a resting cell. Therefore, an adenoviral vector has been utilized for transduction of a gene into differentiated cells, especially into a nervous system cell, when conducting experiments on gene transduction into a primary culture cell or animal body.

In view of the foregoing, it is highly expected that an adenoviral vector will be applicable particularly to gene therapy, because the vector enables an expression of a gene by direct injection or administration into animal body, as well as transduction of a gene into various differentiated and non-differentiated cells including a nervous system cell.

Unlike a retrovirus, however, an adenovirus lacks any positive mechanism for integration into chromosome, resulting in that an expression of a gene in the vector occurs only temporarily. That is, the expression continues only for a few weeks, at most for about 2 months. Thus, when the therapeutic effect has to be maintained, adenovirus should stably exist in cells over long periods so that the adenovirus can continuously produce the expression product of the foreign gene inserted therein.

Recent studies have revealed that E2A gene region in adenoviral genome adversely affects the stability of adenovirus in cells.

Therefore, the present inventors have made extensive investigations to solve the problems mentioned above and have newly found that exists a specific region between the E2A gene region and the L3 gene region of adenovirus, into which a foreign nucleotide can be inserted. The foreign nucleotide may be directly inserted into the specific region in a conventional manner; alternatively, an appropriate linker is firstly inserted therein to construct a necessary restriction enzyme site and then a foreign nucleotide may be inserted into the region between the E2A gene and the L3 gene. The foreign nucleotide to be inserted may be a foreign gene coding for a polypeptide which is intended to be expressed in an animal cell after transfected to the cell, or may be such a foreign nucleotide that can be a substrate for an enzyme naturally existing in the cell.

The present inventors have also found that a new adenoviral vector system for deleting the E2A gene region in the adenoviral genome in an animal cell can be provided by the use of a DNA virus vector having the recombinase-recognizing sequences between the E2A and L3 regions in association with a recombinant DNA viral vector capable of expressing the recombinase gene in the animal cell.

Herein, the term "a recombinase" is used to mean a specific DNA-recombination enzyme which is capable of recognizing a specific DNA sequence comprising several tens of nucleotides to cleave the specific sequence and exchanging the resulting DNA fragments therewith to religate those fragments. Thus, a recombinant adenoviral vector capable of expressing the recombinase is prepared and, another recombinant adenoviral vector is also prepared bearing two copies of a recombinase-recognizing sequence oriented toward the same direction at the both ends in the E2A gene region. When the two adenoviral vectors are co-transfected to a cell, gene reconstruction between the two recombinase-recognizing sequences occurs by the recombinase expressed in the other vector, so that the E2A gene region between the two recombinase-recognizing sequences is cut out as a circular molecule. It is highly expected that the E2A gene region-deleted adenoviral vector becomes markedly more stable as compared to the original adenoviral vector containing the E2A gene region and can be advantageously used for gene therapy.

It was known that a foreign DNA sequence can be inserted into the right portion in the E2A gene region, i.e., the E3 gene region as shown in FIG. 1. However, it was unknown that a specific site, into which a foreign DNA sequence can be inserted, exists in the left portion of the E2A gene region. It has now been discovered according to the present inventors that there is a site between the termination codons for E2A gene and for L3 gene, into which a foreign DNA sequence can be inserted. Thus, it has been revealed for the first time that the two recombinase-recognizing sequences can be inserted in an adenoviral vector to put the E2A gene region therebetween, so that the function of the E2A gene region is not destroyed but the proliferation function inherently possessed by adenovirus is maintained.

Based on the foregoing findings, further studies have been made and the present invention has thus been accomplished.

SUMMARY OF THE INVENTION

Therefore, an object of the present invention is to construct a recombinant adenoviral vector system, wherein an adenoviral vector transduced into an animal cell is present more stably in the cell and hence, a foreign gene inserted into the adenoviral vector at a specific site can be continuously expressed to produce a desired product. Another object of the present invention is to provide such a system for use in gene therapy.

That is, the characteristic features of the present invention are as follows.

(1) A recombinant DNA virus for transfecting an animal cell, bearing a foreign gene and a promoter for regulating expression of the foreign gene, wherein the function of E2A gene is completely deleted.

(2) A recombinant DNA virus according to (1), wherein said DNA virus is an adenovirus.

(3) A recombinant DNA virus according to (1) or (2), wherein a part or all of the E2A gene region is deleted.

(4) A recombinant DNA virus according to any one of (1) to (3), wherein said foreign gene and said promoter for regulating the expression of the foreign gene are inserted in the orientation toward the left side (opposite to the natural transcription orientation of E1A and E1B genes).

(5) A recombinant DNA virus according to any one of (2) to (4), wherein the adenoviral genome has been deleted of 1.3 to 9.3% segment including the E1A gene region.

(6) A recombinant DNA virus according to (5), wherein said foreign gene and said promoter for regulating expression of the foreign gene are inserted at a site wherein said segment has been deleted.

(7) A recombinant DNA virus according to (6), wherein the adenoviral genome has been further deleted of 79.6 to 84.8% segment including the E3 gene region.

(8) A recombinant DNA virus according to any one of (1) to (7), wherein said promoter for regulating expression of the foreign gene is a hybrid promoter (CAG promoter) comprising a cytomegalovirus enhancer, a chicken β-actin promoter, a rabbit β-globin splicing acceptor and poly(A) sequence.

(9) A recombinant DNA virus for transfecting an animal cell, bearing two recombinase-recognizing sequences in the same orientation which are located at both sides of the E2A gene region.

(10) A recombinant DNA virus according to (9), wherein said DNA virus is an adenovirus.

(11) A recombinant DNA virus according to (9) or (10), wherein one of the two recombinase-recognizing sequences is located between the termination codons for E2A gene and for L3 gene, without deleting the function of poly(A)-additional signals of the two genes.

(12) A recombinant DNA virus according to (11), wherein another of the two recombinase-recognizing sequences is located within a frame of from 79.6 to 84.4% of adenoviral genome.

(13) A recombinant DNA virus according to any one of (9) to (12), wherein said recombinase is a recombinase Cre derived from *Escherichia coli* P1 phage.

(14) A recombinant DNA virus according to any one of (9) to (13), wherein each of said recombinase-recognizing sequences is a DNA sequence (SEQ ID NO:1) described below, the DNA sequence being a loxP DNA sequence which is a substrate for a recombinase Cre.

5'-ATAACTTCGTATAGCATACATTATACGAAGTTAT-3'
3'-TATTGAAGCATATCGTATGTAATATGCTTCAATA-5'

(15) A recombinant DNA virus according to any one of (9) to (14), which bears a foreign gene.

(16) A recombinant DNA virus according to (15), which bears a promoter for regulating expression of said foreign gene.

(17) A recombinant DNA virus according to (16), wherein said foreign gene and said promoter for regulating the expression of the foreign gene are inserted in the orientation toward the left side (opposite to the natural transcription orientation of E1A and E1B genes).

(18) A recombinant DNA virus according to any one of (10) to (17), wherein the adenoviral genome has been deleted of 1.3 to 9.3% segment including the E1A gene region.

(19) A recombinant DNA virus according to (18), wherein said foreign gene and said promoter for regulating expression of the foreign gene are inserted at a site wherein said segment has been deleted.

(20) A recombinant DNA virus according to (19), wherein the adenoviral genome has been further deleted of 79.6 to 84.8% segment including the E3 gene region.

(21) A recombinant DNA virus according to any one of (16) to (20), wherein said promoter for regulating expression of the foreign gene is a hybrid promoter (CAG promoter) comprising a cytomegalovirus enhancer, a chicken β-actin promoter, a rabbit β-globin splicing acceptor and poly(A) sequence.

(22) A method for constructing a recombinant DNA virus completely deleted of the function of E2A gene, which comprises the steps of:

transducing into an animal cell line a vector (a) having inserted therein a promoter, a recombinase gene and poly(A) sequence, and a recombinant DNA virus (b) bearing two recombinase-recognizing sequences located in the same orientation at the both sides of the E2A gene region, and cutting out the E2A gene region located between the two recombinase-recognizing sequences.

(23) A method for constructing a recombinant DNA virus according to (22), wherein said recombinant DNA virus (b) is an adenovirus.

(24) A method for constructing a recombinant DNA virus according to (23), wherein said vector (a) is an adenovirus.

(25) A method for constructing a recombinant DNA virus according to any one of (22) to (24), wherein one of the two recombinase-recognizing sequences is located between the termination codons for E2A gene and for L3 gene, without deleting the function of poly(A)-additional signals in the two genes.

(26) A method for constructing a recombinant DNA virus according to any one of (22) to (25), wherein said recombinase is a recombinase Cre derived from *Escherichia coli* P1 phage.

(27) A method for constructing a recombinant DNA virus according to any one of (22) to (26), wherein each of said recombinase-recognizing sequences is a DNA sequence (SEQ ID NO: 1) of loxP which is a substrate for a recombinase Cre.

(28) A method for constructing a recombinant DNA virus according to any one of (22) to (27), wherein said recombinant DNA virus (b) bears a foreign gene.

(29) A method for constructing a recombinant DNA virus according to (28), wherein said recombinant DNA virus (b) further bears a promoter for regulating expression of the foreign gene.

(30) A method for constructing a recombinant DNA virus according to (29), wherein said foreign gene and said promoter for regulating the expression of the foreign gene are inserted in the orientation toward the left side (opposite to the natural transcription orientation of E1A and E1B genes).

(31) A method for constructing a recombinant DNA virus according to any one of (24) to (30), wherein the adenoviral genomes of the vector (a) and the recombinant DNA virus (b) have been deleted of 1.3 to 9.3% segment including the E1A gene region.

(32) A method for constructing a recombinant DNA virus according to (31), wherein said foreign gene and said promoter for regulating expression of the foreign gene of the recombinant DNA virus (b) are inserted at a site wherein said segment has been deleted.

(33) A method for constructing a recombinant DNA virus according to (32), wherein the adenoviral genome of the recombinant DNA virus (b) has been further deleted of 79.6 to 84.8% segment including the E3 gene region.

(34) A method for constructing a recombinant DNA virus according to any one of (29) to (33), wherein said promoter for regulating expression of the foreign gene is a hybrid promoter (CAG promoter) comprising a cytomegalovirus enhancer, a chicken β-actin promoter, a rabbit β-globin splicing acceptor and poly(A) sequence.

(35) A method for constructing a recombinant DNA virus according to (22), wherein the functions of E1A genes both in the vector (a) and the recombinant DNA virus (b) have been deleted, and the animal cell line is an animal cell line which expresses the E1A gene.

(36) A recombinant DNA virus for transfecting an animal cell, which bears a foreign gene inserted between the termination codons for E2A gene and for L3 gene.

DETAILED DESCRIPTION OF THE INVENTION

Figure 1:
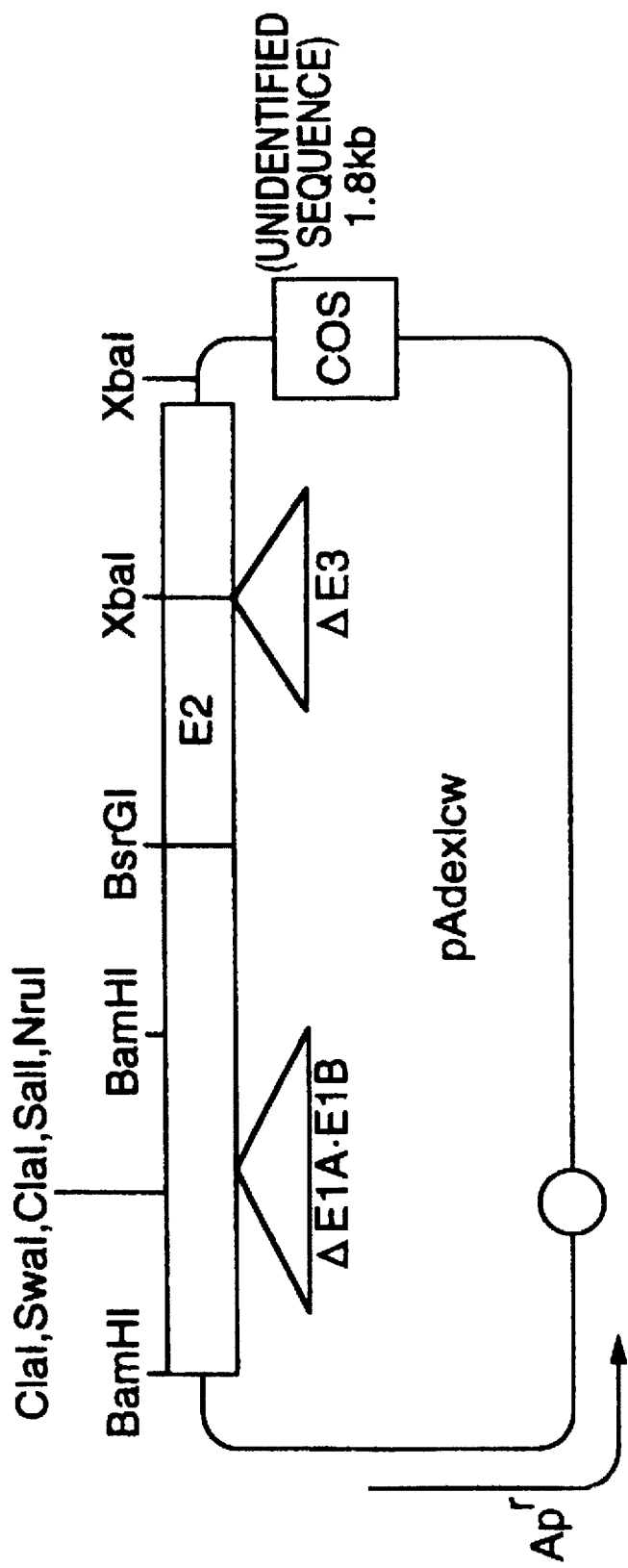
FIG. 1 conceptionally shows the construction of cosmid pAdex1cw.

The present invention will be described below in more detail.

The DNA viral vector used in the present invention may be any vector derived from DNA virus such as an adenovirus that can exist only extrachromosomally after transfected to cells. Such DNA virus-derived vectors may be used without any restriction. Examples of such vectors include an adenoviral vector, a vaccinia viral vector and a papovaviral vector. Hereinafter, the present invention will be described with reference to an adenoviral vector which is a preferred example of the DNA viral vector for transfecting an animal cell and which carries a recombinase gene or a recombinase-recognizing sequence.

The adenovirus used in the present invention is an adenovirus which utilizes an animal as a natural host. A particularly preferred adenovirus is a human adenovirus utilizing a human as a host. Human adenoviral genome is a double-stranded linear DNA of about 36 kbp, and has an unique structure in that the DNA strand has an about 100 bp inverted repeat sequence at the both ends and that the DNA strand has further two 55 k proteins which have been processed from E2B gene product and which are covalently bound to the 5' end of each of both ends of the DNA strand.

The genome of the adenovirus used in the present invention is preferably deleted of the E1 gene region, especially the E1A gene region. This is because, by being deleted of the E1A gene region which is associated with a neoplastic transformation activity of adenovirus, the adenovirus is rendered non-virulent and only a foreign gene integrated in the genome is selectively expressed. The entire E1A gene region is not necessarily deleted, but the deletion of the partial E1A gene region only, especially the 1.3 to 9.3% segment only in the E1A gene region may attain the desired purpose as stated above.

Furthermore, the genome in the adenovirus used in the present invention may also be deleted of the E3 gene region. In particular, the deletion of 79.6 to 84.8% segment in the E3 gene region is preferable, because the segment is not essential for replication of the adenovirus.

Therefore, the adenovirus used in the present invention is characterized in that the adenovirus cannot propagate in usual host cells, except for a human fetal kidney-derived cell line (293 cell line) wherein the E1A and E1B genes are persistently expressed.

However, where an adenovirus has been actually transfected into human or animal adenoviral protein is slightly expressed in the human or animal, because proteins having a function similar to that of E1A protein are present in the human or animal cells. It is known that the thus expressed adenoviral protein causes cell-mediated immune response and as a result cells bearing viral DNA are attacked and destroyed. This is the reason why a E1A or E1B-deleted adenoviral vector can only temporarily express a foreign gene. Yang et al., Nature Genetics, vol. 7, 362–369 (1993) showed that the deletion of E2A gene is effective to prevent the temporary expression and maintain continuously the gene expression. In the method of Yang et al., a temperature-sensitive E2A gene mutant strain is utilized, but when administered to an animal, expression of E2A gene cannot be completely prevented, although the expression is suppressed to the some extent. In order to completely stop the expressing function of the E2A gene, the deletion of the E2A gene region may be considered. However, the expression product of E2A gene is essentially required for replication of the adenoviral genome, and the E2A gene-deleted adenovirus is therefore incapable of proliferating even in 293 cells.

According to the present invention, the recombinant adenovirus bearing recombinase-recognizing sequences at both ends of the E2A gene region together with the adenovirus expressing the recombinase are co-transfected into animal cells. Then, the recombinase expressed in the cells functions in such away that viral particles deleted of the E2A gene region is prepared in the cells. The E2A gene product is supplied in a sufficient amount at least from the adenovirus for expressing the recombinase. The thus obtained E2A gene-deleted virus particle is completely incapable of expressing the E2A gene. Obviously, the period of expressing a desired gene is therefore greatly prolonged.

It is well known that the E2A gene region has at the right side a site into which a foreign sequence may be inserted. Therefore, the recombinase-recognizing sequences may be inserted into the right side. At the left side of the E2A gene region, a specific site between the termination codons for E2A gene and L3 gene is chosen not to prevent proliferation of the recombinant adenovirus transfected. Any of partial deletions of the E2A gene region, L3 gene region and poly(A)-additional signal region is not preferred since proliferation of the resulting recombinant adenovirus is prevented.

As the promoters used in the present invention, there are an animal viral gene promoter and an animal cellular gene promoter. Examples of the animal viral gene promoters include a SV40 gene promoter and an adenovirus major late gene promoter. Examples of the animal cellular gene promoters are a thymidine kinase gene promoter, a metallothionein gene promoter and an immunoglobulin gene promoter. A particularly advantageous promoter in the present invention is CAG promoter. The CAG promoter is a hybrid promoter comprising a cytomegalovirus enhancer, a chicken β-actin promoter, a rabbit β-globin splicing acceptor and poly(A) sequence derived from rabbit β-globin. The CAG promoter is reported as a high expression vector in Japanese Patent KOKAI (Laid-Open) No. 3 (1991)-168087. The CAG promoter may be constructed by cutting out it from a plasmid pCAGGS described in the specification supra at page 13, line 20 to page 20, line 14 and page 22, line 1 to page 25, line 6, with restriction enzymes SalI and Hind III. The thus constructed CAG promoter may be used in the present invention.

The recombinase used in the present invention is a specific DNA recombination enzyme, and capable of recognizing a specific DNA sequence to cleave the sequence and exchanging the resulting DNA fragments therewith to religate those fragments. As such an enzyme, there is recombinase Cre encoded by bacteriophage P1 of $E.\ coli$. The substrate for this enzyme is a DNA sequence of loxP in bacteriophage P1 described in Abremski et al., J. Biol. Chem., 1984, 259, 1509–1514 and Hoess et al., P.N.A.S., 1984, 81, 1026–1029. That is, the loxP DNA sequence is a recognition sequence for the recombinase Cre. Another example of the recombinase is a recombinase encoded by FLP gene derived from yeast 2μ plasmid described in James R. Broarch et al., Cell, 29, 227–234. Furthermore, a recombinase derived from pSR1 plasmid of $Zygosaccharomyces\ rouxii$ may also be employed. This recombinase is encoded by R gene described in Matsuzaki et al., Molecular and Cellular Biology, 8, 955–962 (1988). Among them, bacteriophage P1-derived recombinase Cre is particularly preferred for the present invention.

The recombinase gene, e.g., recombinase Cre gene may be prepared by amplifying the sequence coding the recombinase gene in bacteriophage P1DNA in accordance with a well-known PCR method. The other recombinase genes may be prepared by the PCR method in a similar manner. Primers used in the PCR method are selected so as to amplify the sequence coding the full-length sequence of the recombinase gene. For conveniently constructing the recombinant adenoviral vector, it is preferred to provide the primers with a suitable restriction site at the ends.

The recognition sequence of the recombinase is usually a several tens bp sequence. For example, the loxP sequence is composed of 34 bp, and the nucleotide sequences have all been identified in Abremski et al., J. Biol. Chem., 1984, 259, 1509–1514 and Hoess et al., P.N.A.S., 1984, 81, 1026–1029. Accordingly, the recombinase gene may be chemically synthesized in a conventional manner and provided for use in the present invention.

The poly(A) sequence used in the present invention is not particularly limited, but a rabbit β-globin-derived sequence is particularly preferred.

In the present invention, it is advantageous to introduce a nuclear transfer signal sequence together with the recombinase gene into the adenoviral vector. For example, a nuclear transfer signal of SV40 may be employed. After transfection of the adenoviral vector into cells, the recombinase is produced in the cytoplasm. Thus, in order for the expressed recombinase to act on the recombinase-recognizing sequences in another adenoviral vector, the recombinase must be transferred into the nucleus. The nuclear transfer signal sequence accelerates the transfer of the recombinase into the nucleus, as described in Daniel Kalderon et al., Cell, 39, 499–509 (1984).

The foreign gene used in the present invention are not particularly limited, as far as the gene is expressed under control of the hybrid promoter (CAG promoter) described above or other promoters. In view of practical utility, preferred examples include normal genes which are defective in patients such as adenosine deaminase, dystrophin, low density lipo-protein receptor, α-1 antitrypsin, blood coagulation factor VIII or blood coagulation factor IX, and galactosidase α or β; cytokines such as interleukins 1 through 12, interferon-α, β or γ, tumor necrosis factor-αor β, granulocyte colony stimulating factor, granulocyte macrophage colony stimulating factor, erythropoietin, growth hormone, insulin and insulin-like growth hormone; neurotrophic factors; non-self antigen genes such as allo-HLA (HLA-B7); nucleotide sequences encoding a viral antigen; an antioncogene such as p53, RB, WT-1, NM23 and NF-1; an antisense of oncogene such as Ras sequence; and suicide genes such as thymidine kinase and cytosine deaminase.

The promoter, foreign gene and poly(A) sequence may be inserted in the recombinant adenoviral vector in this order from the upstream or in the inverted order thereof.

Hereunder, the method for constructing the recombinant adenovirus of the present invention is described below.

(1) Firstly, description is made on the method for constructing the recombinant adenoviral vector bearing the two recombinase-recognizing sequences in the same orientation located at both ends of the E2A gene region, a promoter, a foreign gene and a poly(A) sequence. For convenience, the method is described with respect to the embodiment using recombinase Cre as a recombinase, loxP as the recognition sequence and LacZ gene as the foreign gene. However, the following procedures may also apply substantially in a similar manner to the other embodiments using the other recombinases, recognition sequences, promoters and poly (A) sequences.

(a) Construction of cosmid pAdex1CAwt

① Construction of plasmid pCMwCH31 containing CAG promoter

A plasmid pCAGGS bearing CAG promoter (Niwa et al., Gene, 108, 193–200, 1990) is digested with EcoRI. The digestion product is then filled in with Klenow enzyme. Then, the DNA fragments are ligated with SwaI linker using a ligase. The resulting plasmid is digested with SalI. The DNA fragments are filled in with Klenow enzyme followed by ligation with ClaI linker using a ligase. After the thus obtained plasmid is digested with PstI, the DNA fragments are blunted with Klenow enzyme and ligated with XhoI linker using a ligase to obtain plasmid pCMwCH31 containing CAG promoter.

After digestion with respective restriction enzymes, disappearance of the original restriction enzyme sites and the respective linkers inserted are confirmed by electrophoresis on an agarose gel.

② Construction of pAdex1c

The procedures of Example 1 (2), (i) through (iv) hereinafter described are applied to construction of pAdex1c. The procedures are briefly described below.

The following three plasmids are prepared:

a plasmid pUAF0-17D containing 17% segment of the left end in the E1 gene region-deleted adenoviral genome;

a plasmid pUAF0-8 obtained by inserting into pUC19 a 2.8 kb fragment which corresponds to 8% segment of the left end in adenoviral genome and which is prepared by ligating a type 5 adenoviral DNA with BamHI linker and then digesting with HindIII; and, a plasmid pUAF8-17 obtained by inserting a 3.4 kb fragment, which corresponds to 8–17% segment of the left end in adenoviral genome and which is obtained by digesting adenoviral DNA with HindIII, into pUC19 at the HindIII site.

Then, a 454 bp BamHI-ClaI fragment of derived from plasmid pUAF0-8 is ligated with a 2.9 kb HindIII-ClaI fragment derived from plasmid pUAF8-17. The resulting ligation product is inserted into pUC19 at the BamHI/HindIII site to obtain pUAF0-17D.

Furthermore, a type 5 adenoviral DNA is digested with Bst1107 and EcoRI to obtain a 21.6 kb fragment. Separately, a 6.5 kb EcoRI-SalI fragment of pX2W derived from adenoviral genome is prepared.

On the other hand, charomid 9–11 (I. Saito & G. Stark, Proc. Natl. Acad. Sci. U.S.A., 83, 8664–8668, 1986) is digested with Asp718 and BamHI. The DNA fragments are filled in with Klenow enzyme and then subjected to self-ligation. Thereafter, BamHI linker is inserted at the EcoRI site to prepare a charomid chdRBR7-11.

The 2.9 kb BamHI-Bst1107 fragment from plasmid pUAF0-17, the 21.6 kb Bst1107-EcoRI fragment from adenoviral genome and the 6.5 kb EcoRI-SwaI fragment from pX2W are ligated with a DNA fragment obtained by digestion of charomid chdRBR7-11 with EcoRI and Ecl36I. The resulting ligation product is subjected to an in vitro packaging to transfect into DH5α. From the thus obtained transformants, a transformant bearing the objective fragment is isolated and named pAdex1c.

③ Construction of cassette cosmid pAdex1cw

After digesting with ClaI, ethanol precipitation is performed to recover pAdex1c. The recovered pAdex1c is mixed with a synthetic linker (1) (SEQ ID NO: 2) phosphorylated at the 5' end and containing SwaI, ClaI, SalI and NruI sites, as described below.

| Synthetic linker (1): |
| --- |
| 5'-CGATTTAAATCGATTGTCGACTCGCGA-3'<br>3'-TAAATTTAGCTAACAGCTGAGCGCTGC-5' |

The mixture is reacted in a solution containing ATP and T4 DNA ligase overnight to effect ligation. After the ligase is inactivated by heating, the ligation product is digested with SwaI. By the digestion the SwaI fragment is cut out of the product having a plurality of linkers inserted therein to obtain a cosmid wherein only one linker is inserted. Subsequently, the reaction solution is applied on a Spun column (Pharmacia Inc.) to remove small fragments derived from the linkers. Thereafter, ligation is performed using T4 DNA ligase followed by cyclization through self annealing and then by an in vitro packaging. The construction of cosmid DNA prepared from each colony is confirmed by simultaneous digestion with BamHI and NruI. A 483 bp fragment is formed when inserted in the intended orientation and, a 464 bp fragment is formed when inserted in the inverted orientation. It is thus confirmed that the objective cassette cosmid pAdex1cw is obtained, as shown on FIG. 1.

④ Construction of cassette cosmid pAdex1pCAw

The plasmid pCMwCH31 constructed in ① above is concurrently digested with HindIII and ClaI. The DNA fragments are filled in with Klenow enzyme and ligated with PmeI linker which is phosphorylated at the 5' end. After the ligase is inactivated by heating, the ligation product is digested with Psp1406I. By the digestion a Psp1406I fragment is cut out of the product having a plurality of linkers inserted therein to obtain a cosmid wherein one linker is inserted at each of the both ends of DNA fragment. Subsequently, the reaction solution is subjected to agarose gel electrophoresis to excise a gel containing a 2.3 kb DNA fragment. The DNA fragment is recovered from the gel by electrophoresis. Next, pAdex1cw is digested with ClaI and the resulting small fragments are removed by applying on a Spun column (Pharmacia Inc.). The remaining DNA fragment is ligated with the aforesaid 2.3 kb DNA fragment, using T4 DNA ligase. After the ligase is inactivated by heating, ClaI is added to the system to digest the circular cosmid resulting from self annealing. The DNA fragments are used for in vitro packaging.

The construction of cosmid DNA prepared from each colony is confirmed by simultaneous digestion with BamHI and XhoI. Two fragments of 483 bp and 4.8 kb are formed when inserted into the intended orientation. When inserted in the inverted orientation, two fragments of 2.7 kb and 2.5 kb are formed. It is thus confirmed that the objective cassette cosmid pAdex1pCAw is obtained.

⑤ Construction of cassette cosmid pAdex1CAwt [SAIBO KOGAKU (Cell Engineering), 13 (8), 759 (1994)]

After digesting with SwaI, ethanol precipitation is performed to recover pAdex1pCAw. The recovered pAdex1pCAw is mixed with a synthetic linker (2) (SEQ ID NO: 3) phosphorylated at the 5' end and containing ClaI, XbaI, SpeI, PacI, SwaI and ClaI sites as described below.

| Synthetic linker (2): |
| --- |
| 5'-ATCGATTCTAGACTAGTTTAATTAATTTAAATCGAT-3'<br>3'-TAGCTAAGATCTGATCAAATTAATTAAATTTAGCTA-5' |

Figure 2:
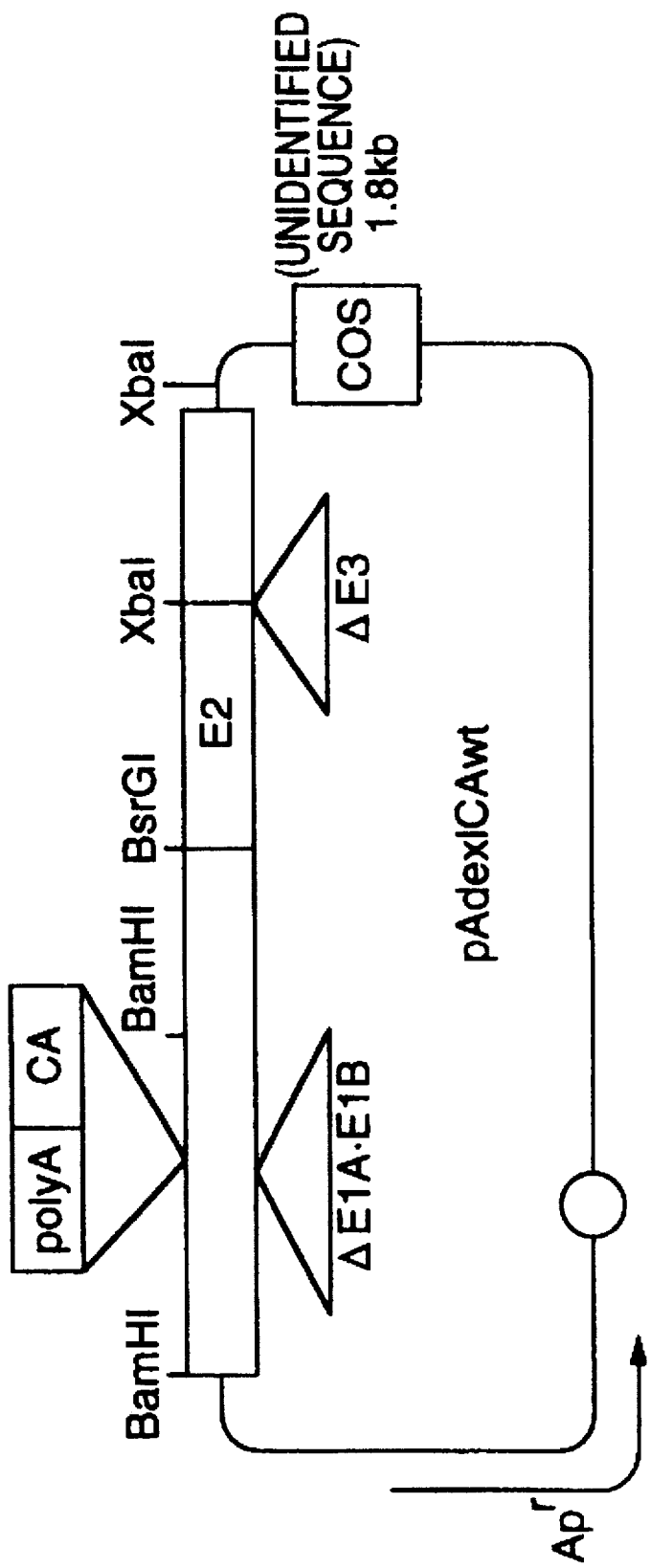
FIG. 2 conceptionally shows the construction of cosmid pAdex1CAwt.

The mixture is reacted in a solution containing ATP and T4 DNA ligase overnight to effect ligation. After the ligase is inactivated by heating, 20 units of PacI is added thereto for digestion. By the digestion the PacI fragment is cut out of the product having a plurality of linkers inserted therein to obtain a cosmid wherein only one linker is inserted. Subsequently, the reaction solution is applied on a Spun column (made by Pharmacia Inc.) to remove small fragments derived from the linkers. Thereafter, ligation is performed overnight in a solution containing T4 DNA ligase followed by cyclization through self annealing. After the ligase is inactivated by heating, the resulting product is used for in vitro packaging. The construction of cosmid DNA prepared from each colony is confirmed by simultaneous digestion with XbaI and XhoI. A 552 bp fragment is formed when inserted in the intended orientation, and a 568 bp fragment is formed when inserted in the inverted orientation. It is thus confirmed that the objective cassette cosmid pAdex1CAwt is obtained, as shown on FIG. 2.

(b) Construction I of loxP-inserted cosmid Construction of cassette cosmid pAdex2L3LCAwt ① Preparation of plasmid pA60X99X After the cassette cosmid pAdex1CAwt is digested with BamHI, the restriction enzyme is inactivated by heating. The resulting DNA fragments are then ligated overnight using T4 DNA ligase. Using this reaction mixture, E. coli DH5α

(GIBCO BRL) is transformed, and plasmid DNA is prepared from the resulting transformant to obtain the objective plasmid pA60X99X.

② Preparation of plasmid pA60X99 (removal of XbaI site other than adenovirus)

Figure 3:
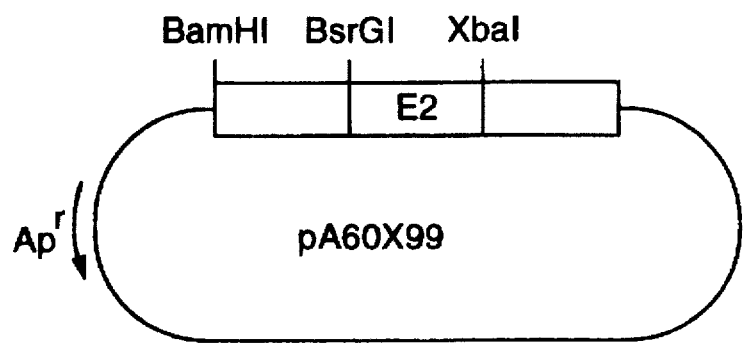
FIG. 3 conceptionally shows the construction of plasmid pA60X99.

After the plasmid pA60X99X is digested with XbaI, the reaction mixture is subjected to electrophoresis on an agarose gel. A gel containing a 23.8 kb DNA fragment, which is digested only at one site of the two XbaI sites, is cut out and the DNA fragment is recovered from the gel by electrophoresis. The fragment is then filled in with Klenow enzyme (Takara Shuzo Co., Ltd.) followed by ligation overnight using T4 DNA ligase. Using this reaction mixture, E. coli DH5α is transformed. From the thus obtained transformants, plasmid DNAs are prepared. These plasmid DNAs are simultaneously digested with BsrGI and XbaI to obtain a 6.2 kb DNA fragment, namely, plasmid pA60X99, as shown in FIG. 3.

③ Preparation of plasmid pA2L60X99 (insertion of loxP into the BsrGI site)

After plasmid pULL2r, which will be prepared as described hereinafter, is digested with XhoI, the both ends of the digestion product are filled in with Klenow enzyme (Takara Shuzo Co., Ltd.). Extraction with phenol-chloroform (1:1) is followed by ethanol precipitation. The precipitates are collected by centrifugation and dissolved in 60 μl of TE buffer. The reaction mixture is mixed and reacted overnight with 5'-end-phosphorylated KpnI linker (Takara Shuzo Co., Ltd.), in a ligase solution (final volume of 50 μl in total) containing ATP and T4 DNA ligase to effect ligation. The ligation product is then digested with Asp718 (Boehringer). The reaction mixture is subjected to agarose gel electrophoresis. A gel containing a 64 bp DNA fragment bearing loxP is cut out and the DNA fragment is recovered from the gel by electrophoresis.

The plasmid pULL2r mentioned above is prepared as follows. Plasmid pUC119 (Takara Shuzo Co., Ltd.) is digested with restriction enzyme Ec1136II followed by a treatment with alkaline phosphatase. Then ligation is performed between the pUC119-Ec1136II fragment and the following synthetic DNA fragment (SEQ ID NO: 4):

```
5'-CGAACGCGTATAACTTCGTATAGCATACATTATACGAAGTTATCTCGAGTCG-3'
3'-GCTTGCGCATATTGAAGCATATCGTATGTAATATGCTTCAATAGAGCTCAGC-5'
``` wherein the underlined sequence indicates the loxP site. The synthetic DNA fragment bears loxP sequence having MluI site and XhoI site at the end thereof and is designed to form NruI site when the MluI and XhoI sites are linked. Thus, plasmid pULL2r in which two of the synthetic DNA fragments have been inserted is obtained.

On the other hand, 10 μg of plasmid pA60X99 is digested with 50 units of BsrGI contained in 50 μl of a solution. The reaction mixture is subjected to agarose gel electrophoresis to cut out a gel containing a 23.8 kb DNA fragment. The DNA fragment is recovered from the gel by electrophoresis. The recovered DNA fragment and the aforesaid 64 bp DNA fragment bearing loxP are reacted overnight in a solution containing ATP and T4 DNA ligase to effect ligation. Sterilized water and BsrGI-reactive buffer are added to the reaction mixture. After the ligase is inactivated by incubation at 70° C. for 10 minutes, circular pA60X99 formed by self-annealing is digested with BsrGI. Using 10 μl of this reaction mixture, E. coli DH5α is transformed. From the thus obtained transformant, plasmid DNA is prepared.

Figure 4:
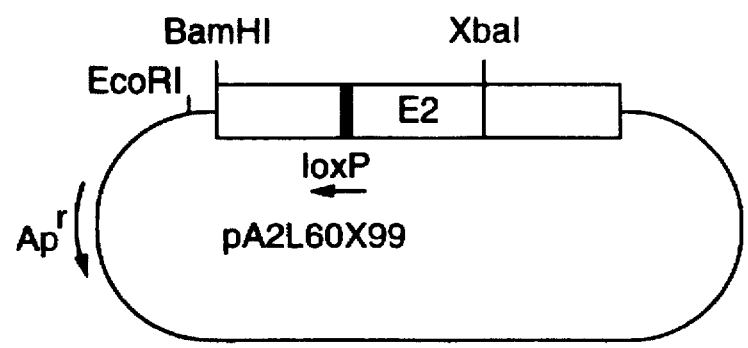
FIG. 4 conceptionally shows the construction of plasmid pA2L60X99.

In order to confirm the orientation of the loxP inserted, the plasmid DNA is simultaneously digested with ApaI and MluI, and the reaction mixture is subjected to agarose gel electrophoresis. Two fragments of 366 bp and 219 bp are formed when inserted in the intended orientation, and two fragments of 334 bp and 251 bp are formed when inserted in the inverted orientation. In the case of digestion with NruI, a 573 bp fragment is formed when inserted in the intended orientation, and a 533 bp fragment is formed when inserted in the inverted orientation. Further, in the case of concurrent digestion with DraI and KpnI, a 320 bp fragment is formed when one loxP is inserted in the intended orientation, and a 384 bp fragment is formed when two loxP sequences are inserted in the intended orientation. The objective plasmid which meets all these three conditions, namely, the objective plasmid pA2L60X99, into which only one loxP has been inserted in the intended orientation, is thus obtained as shown in FIG. 4.

④ Preparation of plasmid pA2L3L6099/insertion of loxP into XbaI site)

After plasmid pULL2r is digested with XhoI in 100 μl of a solution, the both ends of the digestion product are filled in with Klenow enzyme (Takara Shuzo Co., Ltd.). Extraction with phenol-chloroform (1:1) is followed by ethanol precipitation. The precipitates are collected by centrifugation and dissolved in TE buffer. The solution is mixed and reacted overnight with 5'-end-phosphorylated SpeI linker (Takara Shuzo Co., Ltd.), in a ligase solution (final volume of 50 μl in total) containing ATP and T4 DNA ligase to effect ligation. After SpeI is further added for digestion, the reaction mixture is subjected to agarose gel electrophoresis. A gel containing a 64 bp DNA fragment bearing loxP is cut out, and the DNA fragment is recovered from the gel by electrophoresis.

After plasmid pA2L60X99 is digested with XbaI, the reaction mixture is subjected to agarose gel electrophoresis. A gel containing a 23.8 kb DNA fragment is cut out, and the DNA fragment is recovered from the gel by electrophoresis. This DNA fragment is reacted overnight with the aforesaid 64 bp DNA fragment bearing loxP, in a ligase solution containing ATP and T4 DNA ligase to effect ligation. After the ligase is inactivated by heating, the ligation product is treated with XbaI to digest circular pA2L60X99 formed by self-annealing. Using this reaction mixture, E. coli DH5α is transformed. From the thus obtained transformant, plasmid DNA is prepared.

Figure 5:
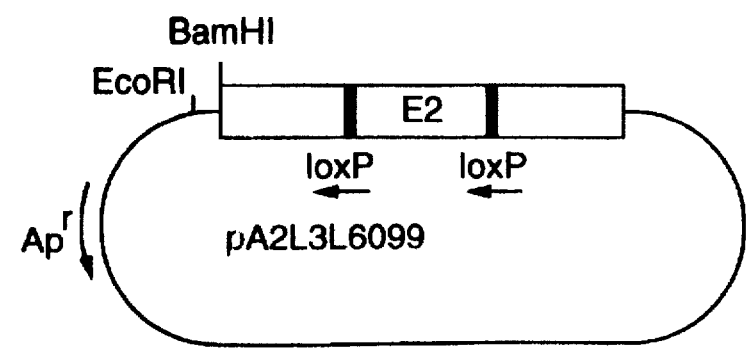
FIG. 5 conceptionally shows the construction of plasmid pA2L3L6099.

In order to confirm the orientation of the loxP inserted, the plasmid DNA is simultaneously digested with BglII and MluI, and the reaction mixture is subjected to agarose gel electrophoresis. Two fragments of 366 bp and 503 bp are formed when inserted in the intended orientation and, two fragments of 398 bp and 471 bp are formed when inserted in the inverted orientation. In the case of simultaneous digestion with ApaI and MluI, a 660 bp fragment is formed when inserted in the intended orientation, and a 628 bp fragment is formed when inserted in the inverted orientation. Further, in the case of concurrent digestion with EcoNI and MluI, a 311 bp fragment is formed when inserted in the intended orientation, and a 343 bp fragment is formed when inserted in the inverted orientation. Further, in the case of concurrent digestion with HpaI and SacI, a 397 bp fragment is formed when one loxP is inserted in the intended orientation, and a 461 bp fragment is formed when two loxP sequences are inserted in the intended orientation. The objective plasmid which meets all these four conditions, namely, the objective plasmid pA2L3L6099, into which only one loxP has been inserted in the intended orientation, is thus obtained as shown in FIG. 5.

(5) Construction of cassette cosmid pAdex2L3LCAwt

After cassette cosmid pAdex1CAwt is digested with Csp45I (Toyobo Co., Ltd.) and then successively with BamHI and with EcoRI in the reaction solution, agarose gel electrophoresis is performed for inspection. A gel containing a 21 kb DNA fragment is cut out, and from the gel the DNA fragment is recovered by electrophoresis. When the 21 kb BamHI-DNA fragment is recovered, digestion with Csp45I and EcoRI is made to prevent contamination with other fragments.

After the plasmid pA2L3L6099 is digested with BamHI, DNA fragments are extracted with phenol-chloroform (1:1). The aqueous layer is subjected to gel filtration using Sephadex G25, which has been previously equilibrated with TE. The recovered DNA fragment is ligated with the aforesaid 21 kb DNA fragment overnight in a solution containing ATP and T4 DNA ligase. After the ligase is inactivated by heating, the cassette cosmid is used for an in vitro packaging.

That is, an aliquot of the cassette cosmid is subjected to an in vitro packaging using Gigapack XL kit (Stratagene Co., Ltd.), and the remaining cosmid is lyophilized at −80° C. Since Gigapack XL bit provides a low package efficiency for a 42 kb or less cosmid, the kit can select at a certain extent a cosmid that has become a larger size by including an insert sequence. In the present invention, when 10 colonies are picked up, most of them include the insert sequence. Therefore, the objective clone (namely, clone with which viral genome has been correctly ligated) can be readily obtained. The cosmid is treated in a conventional manner described in Izumu Saito, et al., JIKKEN IGAKU (Experimental Medicine), 7, 183–187 (1989).

The packaged cosmid is transfected into *E. coli* DH5α (GIBCO BRL). That is, the cosmid is inoculated on each of Ap⁺ agar plates (supplemented with ampicillin) and Ap⁺ LB (pool) at various concentrations, followed by incubation overnight. The miniprep DNA from the pool is extracted and prepared to examine a ratio of the cosmid having the insert sequence by digestion with restriction enzyme DraI. The colony is picked up together with the agar plate, and cultured in Ap⁺ LB overnight to prepare the miniprep DNA. Next, the structure of the cosmid prepared from each colony is confirmed by digestion with DraI. When inserted in the intended orientation, a 891 bp fragment is formed. When inserted in the inverted orientation, a 1.4 kb fragment is formed. According to this procedure, the objective cassette cosmid pAdex2L3LCAwt is obtained.

That is, a plasmid bearing the expression unit but deleted of most adenovirus DNA is prepared with NruI and ligase, and a DNA fragment is then prepared from the plasmid for final confirmation of cDNA cloning.

(c) Construction II of loxP-inserted cosmid Construction of cassette cosmid pAdex2LA3LCAwt ① Preparation of plasmid pUCA6065

After pA60X99 is digested with BamHI and PstI, the reaction mixture is subjected to agarose gel electrophoresis to cut out a gel containing a 1.7 kb DNA fragment bearing BsrGI site. From the gel the DNA fragment is recovered by electrophoresis. In a similar manner, pUC19 is digested with BamHI and PstI to recover a 2.7 kb DNA fragment. Then, the two fragments are added to a buffer for ligase reaction, and ATP and T4 DNA ligase are further added thereto. The reaction is carried out overnight to effect ligation. Using the reaction mixture, *E. coli* DH5α is transformed and plasmid DNA is prepared from the resulting transformant to obtain the objective plasmid pUCA6065.

② Preparation of plasmid p2LA6065

The plasmid pUCA6065 is digested with BamHI and AflIII to prepare a 780 bp DNA fragment. Further, the same plasmid is digested with BamHI and BsrGI to prepare a 3.6 kb DNA fragment. These two fragments are mixed with linker DNA (SEQ ID NO: 11) bearing loxP as shown below.

```
5'-CATGTAATTT AAATCTCGAG ATAACTTCGT ATAATGTATG CTATACGAAG TTATACGCGT
3'-ATTAAA TTTAGAGCTC TATTGAAGCA TATTACATAC GATATGCTTC AATATGCGCA
ATTTAAATGT AAAAATAATG TACTAGAGAC ACTTTCAATA AAGGCAAATG CTTTTATTT-3'
TAAATTTACA TTTTTATTAC ATGATCTCTG TGAAAGTTAT TTCCGTTTAC GAAAATAAAC ATG-
                                                                     5'
```

The mixture is added to a buffer for ligase reaction, and ATP and T4 DNA ligase are further added thereto. The reaction is carried out overnight to effect ligation. Using the reaction mixture, *E. coli* DH5α is transformed, and a plasmid DNA is prepared from the resulting transformant. Thus, the objective plasmid p2LA6065, in which one linker DNA has been inserted, is obtained.

③ Preparation of plasmid pA2LA3L6099

Plasmid p2LA6065 is digested with BamHI and SfiI (or BglI) to prepare a 1.5 kb DNA fragment. Further, plasmid pA2L3L6099 is digested with BamHI and SfiI to prepare about 22 kb DNA fragment. These two fragments are added to a buffer for ligase reaction, and ATP and T4 DNA ligase are further added thereto. The reaction is carried out overnight to effect ligation. Using the reaction mixture, *E. coli* DH5α is transformed, and a plasmid DNA is prepared from the resulting transformant. Thus, the objective plasmid pA2LA3L6099 is obtained.

④ Construction of cosmid cassette pAdex2LA3LCAwt

Cosmid pAdex2LA3LACAwt is constructed from pA2LA3L6099 and pAdex1CAwt in a manner similar to the construction of pAdex2L3LCAwt described in (b)⑤ above.

(d) Construction III of loxP-inserted cosmid Construction of cassette cosmid pAdex2LD3LCAwt ① Preparation of plasmid pHSGA6065

After pA60X99 is digested with BamHI and PstI, the reaction mixture is subjected to agarose gel electrophoresis. A gel containing a 1.7 kb DNA fragment bearing BsrGI site is cut out. From the gel the DNA fragment is recovered by electrophoresis. Plasmid pHSG299 (Takara Shuzo Co., Ltd.) is digested with BamHI and PstI. In a similar manner, a 2.7 kb DNA fragment is recovered. Then, the two fragments are added to a buffer for ligase reaction, and ATP and T4 DNA ligase are further added thereto. The reaction is carried out overnight to effect ligation. Using the reaction mixture, *E. coli* DH5α is transformed, and a plasmid DNA is prepared from the resulting transformant to obtain the objective plasmid pHSGA6065.

②  Preparation of plasmid p2LD6065

The plasmid pHSGA6065 is digested with BsrGI and DraI to prepare a 4.4 kb DNA fragment. The fragment is mixed with linker DNA (SEQ ID NO: 12) bearing loxP as shown below.

```
5'-GTACACTCTC GGGTGATTAT TTACCCCCAC CCTTGCCGTC TGCGCCGATT TAAATCTCGA
   3'-TGAGAG CCCACTAATA AATGGGGGTG GGAACGGCAG ACGCGGCTAA ATTTAGAGCT
GATAACTTCG TATAATGTAT GCTATACGAA GTTATACGCG TATTTAAATC CGTTT-3'
CTATTGAAGC ATATTACATA CGATATGCTT CAATATGCGC ATAAATTTAG GCAAA-5'
```

The mixture is added to a buffer for ligase reaction, and ATP and T4 DNA ligase are further added thereto. The reaction is carried out overnight to effect ligation. Using the reaction mixture, *E. coli* DH5α is transformed, and a plasmid DNA is prepared from the resulting transformant. Thus, the objective plasmid p2LD6065, in which one linker DNA has been inserted, is obtained.

③ Preparation of plasmid pA2LD3L6099

Plasmid p2LD6065 is digested with BamHI and SfiI (or BglI) to prepare a 1.5 kb DNA fragment. Further, plasmid pA2L3L6099 is digested with BamHI and SfiI to prepare about 22 kb DNA fragment. These two fragments are added to a buffer for ligase reaction, and ATP and T4 DNA ligase are further added thereto. The reaction is carried out overnight to effect ligation. Using the reaction mixture, *E. coli* DH5α is transformed, and a plasmid DNA is prepared from the resulting transformant. Thus, the objective plasmid pA2LD3L6099 is obtained.

④ Construction of cosmid cassette pAdex2LD3LCAwt

Cosmid plasmid pAdex2LD3LACAwt is constructed from pA2LD3L6099 and pAdex1CAwt in a manner similar to the construction of pAdex2L3LCAwt described in (b)⑤ above.

(e) Preparation of adenoviral DNA-terminal protein complex (Ad5 d1X DNA-TPC and Adex1CANLacZ DNA-TPC)

① As an adenovirus DNA, Ad5 d1X (I. Saito et al., J. Virology, vol. 54, 711–719 (1985)) or Adex1CANLacZ is used. Ad5 d1X DNA and Adex1CANLacZ are transfected into HeLa cells (at the amount of 10 Roux tubes) and 293 cells, respectively, followed by incubation.

That is, the viral solution (~$10^9$ PFU/ml) of Ad5-d1X or Adex1CANLacZ is transfected at the amount of 0.2 ml/Roux tube. Three days after, the cells peeled off are collected by centrifugation. Most of the adenovirus particles do not exist in the medium, but in the nucleus. Therefore, the virus is advantageously purified from the infected cells.

The following procedures are aseptically performed.

② The thus obtained cells are suspended in Tris-HCl (pH 8.0), and sonicated using a sealed type sonicator to destroy the cells thereby to release the virus.

③ After the thus obtained cell debris is removed by centrifugation, the supernatant is overlaid on cesium chloride solution (specific gravity of 1.43) charged in a ultracentrifuging machine SW28 tube, followed by concentration with cushion centrifugation.

④ The virus layer immediately below the interface is transferred to a SW50.1 tube. In general, the virus layer immediately below the interface is visually observed, and 5 ml of cesium chloride solution containing the virus layer and layer therebelow is collected. At the same time, another tube is filled up with the cesium chloride solution (specific gravity of 1.34).

These tubes are centrifuged at 4° C. overnight at 35 k rpm. Then, the thus formed white band indicating virus existence is collected, and transferred onto a tube which previously formed gradients. The tube is further subjected to ultracentrifugation at 4° C. for 4 hours at 35 k rpm.

⑤ The white band indicating virus existence is collected, and mixed with 8M guanidine hydrochloride at the same amount. Furthermore, 4M guanidine hydrochloride-saturated cesium chloride is added to the mixture. The resulting mixture is filled in a VTi65 tube. The particle protein is denatured with 4M guanidine hydrochloride to cause dissociation, whereby a DNA-TPC complex is released.

⑥ The tube described above is subjected to ultracentrifugation at 15° C. overnight at 55 k rpm, followed by fractionation with 0.2 ml. From each of the fractions, 1 μl is packed up, and mixed with 1 μg/ml of ethidium bromide aqueous solution to confirm the presence or absence of a DNA with fluorescence-staining. Two or three fractions containing the DNA are collected.

⑦ The fractions are dialyzed twice against 500 ml of TE overnight, and then stored at −80° C. The amount of the thus obtained Ad5d1X DNA-TPC complex or Adex1CANLacZ DNA-TPC complex is determined on the basis of $OD_{260}$ value in a conventional method for determining DNA.

⑧ The resulting Ad5d1X DNA-TPC complex or Adex1CANLacZ DNA-TPC complex is digested with AgeI at a sufficient amount for 2 hours. After gel filtration through Sephadex G25 column, the complex is stored at −80° C. for constructing recombinant adenovirus bearing loxP at the following step.

(f) Preparation of loxP-inserted recombinant adenoviruses

NLacZ gene is obtained by adding a nuclear transfer signal sequence of SV40 to 5'-end of LacZ gene of *E. coli*.

① Each one of 6 cm and 10 cm diameter Petri dishes is charged with 293 cells cultured in DME supplemented with 10% FCS.

②-1. Constructions of Ad5d1X2L3L and Adex2L3LCANLacZ

After 8 μg of cosmid pAdex2L3LCAwt DNA having loxP and an expression unit introduced therein is mixed with 1 μg of Ad5d1X DNA-TPC complex previously digested with AgeI or 1 μg of Adex1CANLacZ DNA-TPC complex previously digested with AgeI, transfection is effected on the 6 cm Petri dish using Celfect Kit (Pharmacia) according to a calcium phosphate method. That is, the mixture is dropped onto the medium in the 6 cm Petri dish, and the incubation is continued.

After the overnight incubation (for about 16 hours), the culture medium is exchanged in the next morning. Then, in the evening, the medium containing cells is poured with 5% FCS-containing DME into wells in three 96-well collagen coated plates (non-diluted stock solution, 10-fold diluted, and 100-fold diluted solutions) at the amount of 0.1 ml/well. In order to avoid a significant difference in the cell count between each plate, one third of the 293 cells harvested from 10 cm Petri dish are added on each of two diluted solution plates.

②-2. Constructions of Ad5d1X2LA3L and Adex2LA3LCANLacZ

After 8 μg of cosmid pAdex2LA3LCAwt DNA having loxP and an expression unit introduced therein is mixed with 1 μg of Ad5d1X DNA-TPC complex previously digested with AgeI or 1 μg of Adex1CANLacZ DNA-TPC complex previously digested with AgeI, transfection is effected on the 6 cm Petri dish using Celfect Kit (Pharmacia) according to a calcium phosphate method. That is, the mixture is dropped onto the medium in the 6 cm Petri dish, and the incubation is continued.

After the overnight incubation (for about 16 hours), the culture medium is exchanged in the next morning. Then, in the evening, the medium containing cells is poured with 5% FCS-containing DME into wells in three 96-well collagen coated plates (non-diluted stock solution, 10-fold diluted, and 100-fold diluted solution) at the amount of 0.1 ml/well. In order to avoid a significant difference in the cell count between each plate, one third of the 293 cells harvested from 10 cm Petri dish are added on each of two diluted solution plates.

②-3. Constructions of Ad5d1X2LD3L and Adex2LD3LCANLacZ

After 8 μg of cosmid pAdex2LD3LCAwt DNA inserted with having loxP and an expression unit introduced therein is mixed with 1 μg of Ad5d1X DNA-TPC complex previously digested with AgeI or 1 μg of Adex1CANLacZ DNA-TPC complex previously digested with AgeI, transfection is effected on the 6 cm Petri dish using Celfect Kit (Pharmacia) according to a calcium phosphate method. That is, the mixture is dropped onto the medium in the 6 cm Petri dish, and the incubation is continued.

After the overnight incubation (for about 16 hours), the culture medium is exchanged in the next morning. Then, in the evening, the medium containing cells is poured with 5% FCS-containing DME into wells in three 96-well collagen coated plates (non-diluted stock solution, 10-fold diluted, and 100-fold diluted solution) at the amount of 0.1 ml/well. In order to avoid a significant difference in the cell count between each plate, one third of the 293 cells harvested from 10 cm Petri dish are added on each of two diluted solution plates.

③ Three or four days after and eight or ten days after, 50 μl of 10% FCS-containing DME is further added to each well. When the 293 cell lines become thin, 10% FCS-containing DME should be earlier added to the well.

The wells, wherein the virus has propagated and the cells are dead, are observed in 7 to 20 days. From every wells wherein the cells are completely dead, the culture media containing dead cells is transferred with a sterile pasteur pipette into a 1.5 ml sterilized tube. The tube is quickly lyophilized and stored at −80° C.

④ The observation is finished in 15 to 25 days. About ten (10) tubes are selected from the tubes charged with the culture media containing the cells which are dead at a relatively late stage. After ultrasonication, centrifugation is conducted at 5 k rpm for 10 minutes. The resulting supernatant is stored for use as a first seed at −80° C.

The wells in which the virus has started to propagate at an earlier stage suggest a higher probability of mixed infections with a plurality of virus strains.

⑤ The 293 cell lines are charged in a 24-well plate, and 5% FCS-DME (0.4 ml/well) and 10 μl of the first viral seed are added to wells in duplicate.

⑥ Where the cells are completely dead in about 3 days, the supernatant is obtained from one of the duplicate wells by ultrasonication and centrifugation in a manner similar to the procedures for preparing the first viral seed as described above. The thus obtained supernatant is stored at −80° C. for use as a second seed. The dead cells in another well of the duplicate wells are centrifuged at 5000 rpm for 5 minutes, and the supernatant is discarded. The cells alone are stored at −80° C. (cell pack). The cell packs of 10 viral strains are collected, and the entire DNA is extracted from the infected cells according to the following procedures. To each cell pack are added 400 μl of TNE for cell DNA (50 mM Tris-HCl, pH 7.5, 100 mM NaCl, 10 mM EDTA), 4 μl of proteinase K (10 mg/ml) and 4 μl of 10% SDS.

⑦ After treating at 50° C. for an hour, extraction is performed twice with phenol-chloroform and twice with chloroform, and then ethanol precipitation is performed. The nucleic acid recovered by ethanol precipitation is dissolved in 50 μl of TE containing 20 μg/ml ribonuclease.

After 15 μl of the solution is digested with XhoI which cleaves the expression unit and which recognizes a site contains CG, the digested product is subjected, together with the XhoI-digested product of an expression cosmid cassette, to electrophoresis overnight on agarose gel having a length of about 15 cm. The patterns thus obtained are compared. Selected is the clone which has a band indicating the cleavage pattern of two inserted loxP sequences resulted from the digestion with XhoI recognizing the site in loxP. The clones which provide many bands indicating undetermined DNA sequences are discarded, since there is a possibility that the clones would be contaminated with the virus having deletions.

Using the thus obtained loxP-inserted recombinant adenovirus Ad5d1X2L3L, Ad5d1X2LA3L or Ad5d1X2LD3L and a cosmid bearing the objective foreign nucleotide expression unit, a recombinant adenovirus, in which the objective foreign gene expression unit and loxP have been inserted, can be constructed according to known methods for constructing recombinant adenovirus, for example, COS-TPC method described in JIKKEN IGAKU BESSATSU (Experimental Medicine, Extra Issue), Bio Manual Series No. 4, IDENSHI DONYU-TO-HATSUGEN KAISEKI-HO (Study on Gene Transduction and Expression), pages 43–58).

(g) Construction of E2A gene-deleted adenovirus and confirmation of its structure Recombinant adenoviruses Adex2L3LCANLacZ and Adex1CANCre are transfected into 293 cells at moi of 10 and 3, respectively, followed by incubation. Four days after, the cells are recovered, and DNA is prepared by the procedures described hereinabove. It is confirmed by the two methods, i.e., digestion with SmaI and PCR as described below, that the formed Adexd123CANLacZ has such a structure that the E2A gene-containing region located between the two loxP sequences has been cut out.

It can be similarly confirmed also on Adex2LA3LCANLacZ and Adex2LD3LCANlacZ that these recombinant adenoviruses have the desired structure.

1. Digestion with SmaI

Digestion with SmaI followed by gel electrophoresis results in excision of the region located between the two loxP sequences to form a 4.7 kb fragment. From comparison in band density between the above band of the 4.7 kb fragment and the band of 4.45 kb commonly observed in Adex2L3LCANLacZ, Adex1CANCre and Adexd123CANLacZ, it is determined about what percentage in the recovered recombinant adenovirus will be Adexd123CANLacZ.

2. Confirmation by PCR

PCR reaction is conducted under conventional conditions, using 0.1 ng of the prepared DNA as a template. The product is analyzed by electrophoresis on an agarose gel. Primers employed are preferably Oligonucleotide (1) (SEQ ID NO: 5), Oligonucleotide (2) (SEQ ID NO: 6), Oligonucleotide (3) (SEQ ID NO: 7) and Oligonucleotide (4) (SEQ ID NO: 8), as shown below.

| Oligonucleotide (1) |
|---|
| 5'-CAACTCCATGCTCAACAGTCCCCAGGTACA-3' |

| Oligonucleotide (2) |
|---|
| 5'-GATTTTTAAACGGCGCAGACGGCAAG-3' |

| Oligonucleotide (3) |
|---|
| 5'-GTGAGCTTAGAAAACCCTTAG-3' |

| Oligonucleotide (4) |
|---|
| 5'-AGATACCCCTTTTGCACTGGTGCAAGTTAAC-3' |

As a reaction solution for PCR, preferred is 10 mM Tris-HCl (pH 8.3) containing 50 mM KCl, 1.5 mM MgCl, 0.2 mM dNTP mixture and 0.2 µM each of primer, 0.1 ng of template DNA and 0.5 unit of Taq polymerase.

Figure 6:
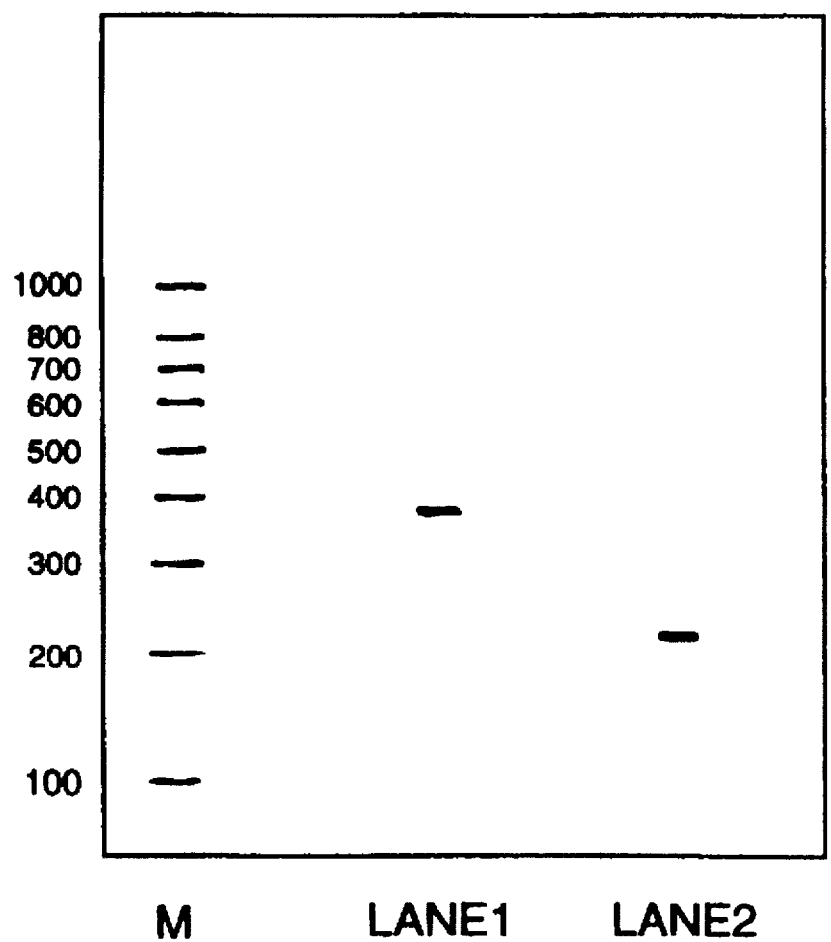
FIG. 6 shows the results obtained by co-transfecting 293 cells with recombinant adenovirus Adex2L3LCANLacZ and Adex1CANCre, recovering the co-transfected cells, extracting the DNA and performing polymerase chain reaction (PCR) using the extracted DNA as a template, wherein Lane 1 shows the profile of electrophoresis using primers (1) and (4) and, Lane 2 shows the profile of electrophoresis using primers (2) and (3).

A preferred example of the reaction conditions for PCR is 1.5 minute for dissociation of double strand at 95° C., 1.0 minute for annealing at 64° C., 1.0 minute for chain extension reaction at 70° C., and reaction cycle of 30 times.

Where Oligonucleotides (1) and (4) are employed as primers, a band which is assumed to show a 393 bp sequence is detected, indicating that Adexd123CANLacZ deleted of E2A gene is present. Where Oligonucleotides (2) and (3) are used as primers, a band which is assumed to show a 221 bp sequence is detected, supporting the presence of circular E2A gene cut out by the Cre gene product. It is thus revealed that Adexd123CANLacZ in which the E2A gene region located between the loxP sequences has been excised from Adex2L3LCANLacZ is formed, as shown in FIG. 6. (2) Next, description will be made on a method for constructing the recombinant adenoviral vector bearing a promoter, a recombinase gene and poly(A) sequence.

In the following method, an embodiment using recombinase Cre gene as the recombinase gene is given as one example. However, the method is applicable to the other embodiments using other recombinase genes.

① Recombinase Cre gene prepared by PCR and plasmid pUC19 (Takara Shuzo Co., Ltd.) are simultaneously digested with restriction enzymes PstI and XbaI (Takara Shuzo Co., Ltd.), respectively. The DNA fragments are mixed and ligated with each other to obtain plasmid pUCCre having recombinase Cre gene inserted therein.

② The cassette cosmid pAdex1CAwt containing CAG promoter is digested with restriction enzyme SwaI (Boehringer), and the resulting DNA fragment is mixed with the DNA fragment obtained by simultaneous digestion of pUCCre with restriction enzymes PstI and XbaI (Takara Shuzo Co., Ltd.), followed by blunting with Klenow enzyme (Takara Shuzo Co., Ltd.). Then, the cassette cosmid is precipitated and ligated using T4 DNA ligase. The cassette cosmid having recombinase Cre gene inserted therein is thus obtained.

Where a promoter other than CAG promoter is employed, the following procedure is advantageous. Firstly, the 1.9 kb E3 region and the 2.9 kb E1A.E1B region, which are unnecessary for replication, are deleted from the full length adenoviral genome (36 kb) to form a cassette cosmid having about 31 kb genome DNA. On the other hand, a plasmid bearing a promoter recombinase Cre gene and poly(A) sequence is prepared. Digestion treatment of the above cassette cosmid and plasmid with appropriate restriction enzymes to obtain a cassette cosmid having the recombinase Cre gene expression unit inserted into the adenoviral genome at the E1A.E1B region-deleted site.

③ The thus obtained cassette cosmid is subjected to an in vitro packaging, using Gigapack XL (Stratagene Co., Ltd.).

④ On the other hand, adenoviral DNA-terminal protein complex (Ad5 d1X DNA-TPC) is prepared. As an adenovirus DNA, Ad5 d1X (I. Saito et al., J. Virology, vol. 54, 711–719 (1985)) is used. Ad5 d1X DNA is transfected into HeLa cells at the amount of 10 Roux tubes, followed by incubation. The viral particles are recovered, and then treated with guanidine hydrochloride. DNA-TPC is separated and recovered by ultracentrifugation.

The thus obtained Ad5d1X DNA-TPC complex is digested with EcoT22I at a sufficient amount for use in the following step.

⑤ In the final step, the cassette cosmid having recombinase Cre gene inserted therein is mixed with Ad5d1X DNA-TPC complex previously digested with EcoT22I, and then transfection is effected using Celfect Kit (Pharmacia) according to the calcium phosphate method. The viral solution is recovered from the medium in which the cells are dead due to proliferation of virus. The recombinant adenoviral vector bearing the promoter, recombinase gene and poly(A) sequence is thus obtained.

According to the present invention, the recombinant adenovirus bearing the objective foreign gene expression unit and completely deleted of the function of E2A gene may be effectively used for the treatment of various diseases including genetic diseases. In more detail, a high titer viral solution containing the recombinant adenovirus of the present invention is appropriately diluted, and the diluted solution may be administered through an appropriate route, e.g., topically (central nervous system, portal vein), orally (using enteric coating), by inhalation, subcutaneously, and the like.

Hereinafter, the present invention will be described in more detail by referring to Examples and Reference Examples, but is not deemed to be limited thereto.

In the Examples, various procedures for manipulating phages, plasmids, DNAs, various enzymes, E. coli, culture cells and the like were carried out, unless otherwise indicated, according to modifications of the methods as described in Molecular Cloning, A Laboratory Manual, edited by T. Maniatis et al., second edition (1989), Cold Spring Harbor Laboratory. DNA restriction enzymes and modified enzymes were purchased from Takara Shuzo Co., Ltd., New England Biolabs (NEB), Stratagene or Boehringer, and used in accordance with their instructions.

EXAMPLE 1

Construction of pAdex1CAwt

① Construction of plasmid pCMwCH31 containing CAG promoter

A plasmid pCAGGS bearing CAG promoter (Niwa et al., Gene, 108, 193–200, 1990) was digested with EcoRI. The DNA fragment was then filled in with Klenow enzyme. Thereafter, the DNA fragments were ligated with SwaI linker using a ligase. The resulting plasmid was digested with SalI. The DNA fragment was blunted with Klenow enzyme followed by ligation with ClaI linker using a ligase. After the thus obtained plasmid was digested with PstI, the DNA fragment was blunted with Klenow enzyme and ligated with XhoI linker using a ligase. After digestion with respective restriction enzymes, it was confirmed by agarose gel electrophoresis that the original restriction enzyme site disappeared and each linker was inserted.

② Construction of pAdex1c (i) Construction of plasmid pUAF0-17D containing 17% segment in the left end of adenoviral genome deleted of the E1 gene region Type 5 adenoviral DNA was blunted with S1 nuclease and BamH linker was ligated at the blunt end. Digestion with HindIII gave an objective DNA fragment which has 2.8 kb and corresponds to 8% of the left end in the adenoviral genome. The fragment was separated and recovered by agarose gel electrophoresis, and inserted into the BamHI/ HindIII site of pUC19 previously digested with BamHI/ HindIII. The thus obtained plasmid was named pUAF0-8.

(ii) Adenoviral DNA was digested with HindIII. An objective 3.4 kb DNA fragment, which corresponds to 8–17% of the left end in the adenoviral genome, was recovered from the gel and inserted into pUC19 at the HindIII site. The thus obtained plasmid was named pUAF8-17.

In the plasmid pUAF0-8, the PvuII site corresponding to a base number 454 was converted to the ClaI site using ClaI linker. The base number referred to herein is derived from a base number in adenoviral DNA. The plasmid was then digested with BamHI/ClaI. The 454 bp BamHI/ClaI fragment was recovered by agarose gel electrophoresis.

In the plasmid pUAF8-17, the BglII site corresponding to a base number 3328 was converted to the ClaI site using ClaI linker. The plasmid was then digested with BamHI/ClaI. The 2.9 kb BamHI/ClaI fragment was recovered by agarose gel electrophoresis.

The 454 bp BamHI-ClaI fragment derived from plasmid pUAF0-8 was ligated with the 2.9 kb HindIII-ClaI fragment derived from plasmid pUAF8-17. The resulting ligation product was inserted into pUC19 at the BamHI/HindIII site. The thus obtained plasmid was named pUAF0-17D. The plasmid contains 17% of the left end in the E1 gene region-deleted adenoviral genome.

(iii) Preparation of Bst1107-EcoRI fragment (21.6 kb) of adenoviral genome

Type 5 adenoviral DNA was digested with Bst1107 and EcoRI. After separation by agarose gel electrophoresis, an objective 21.6 kb fragment was recovered.

(iv) Preparation of EcoRI-SalI fragment (6.5 kb) of adenoviral genome

The SalI site of pX2S (I. Saito et al., J. Virology, vol. 54, 711–719 (1985)) was converted into the SwaI site, using SwaI linker. The resulting pX2W was digested with EcoRI and SwaI. After the DNA fragment was separated by agarose gel electrophoresis, an objective 6.5 kb fragment was recovered.

(v) Preparation of charomid chdRBR7-11

In order to remove KpnI, SmaI and BamHI sites in charomid 9–11 (I. Saito & G. Stark, Proc. Natl. Acad. Sci. U.S.A., 83, 8664–8668, 1986), charomid 9–11 was digested with Asp718 and BamHI. The resulting DNA fragments were filled in with Klenow enzyme and then subjected to self-ligation. Transformation using the ligated sequence gave the objective charomid, which was named charomid 6–11. BamHI linker was inserted into charomid 6–11 at the EcoRI site. The thus obtained charomid was named charomid chdRBR7-11.

(vi) Preparation of pAdex1c

The 2.9 kb BamHI-Bst1107 fragment from pUAF0-17, the 21.6 kb Bst1107-EcoRI fragment from adenoviral genome and the 6.5 kb EcoRI-SwaI fragment from pX2W were ligated with chdRBR7-11 previously digested with EcoRI and Ecl136I. The ligated sequence was subjected to an in vitro packaging, and transfected into E. coli DH5α. From the transformants, an objective cosmid was isolated and named pAdex1c.

(3) Construction of cassette cosmid pAdex1cw

After digesting with 20 units of ClaI, ethanol precipitation was performed to recover pAdex1c. The recovered pAdex1(1 μg) was mixed with 0.01 μg of a synthetic linker (1) (SEQ ID NO: 2) phosphorylated at the 5' end and containing SwaI, ClaI, SalI and NruI sites as described below.

| Synthetic linker (1): |
|---|
| 5'-CGATTTAAATCGATTGTCGACTCGCGA-3' |
| 3'-TAAATTTAGCTAACAGCTGAGCGCTGC-5' |

The mixture was reacted overnight in total 18 μl of a solution containing ATP and T4 DNA ligase to effect ligation. After the ligase was inactivated by incubation at 70° C. for 10 minutes, 20 units of SwaI was added thereto for digestion. According to the digestion, the SwaI fragment was cut out of the product having a plurality of linkers inserted therein to obtain a cosmid wherein only one linker was inserted. Subsequently, the reaction solution was applied on a Spun column (Pharmacia Inc.) to remove small fragments derived from the linkers. Thereafter, ligation was performed overnight in total 18 μl of a solution containing ATP and T4 DNA ligase, followed by cyclization through self annealing. After the ligase was inactivated by incubation at 70° C. for 10 minutes, 1 μl of the resulting product was used for an in vitro packaging.

The construction of the cosmid DNA prepared from each colony was confirmed by simultaneous digestion with BamHI and NruI. A 483 bp fragment is formed when inserted in the intended orientation and, a 464 bp fragment is formed when inserted in the inverted orientation. It was thus confirmed that the objective cassette cosmid pAdex1cw was obtained, as shown on FIG. 1.

④ Construction of cassette cosmid pAdex1pCAw

The plasmid pCMwCH31 constructed in ① above was concurrently digested with HindIII and ClaI. The DNA fragments were filled in with Klenow enzyme and ligated with PmeI linker previously phosphorylated at the 5' end. After the ligase was inactivated by incubation at 70° C. for 10 minutes, the ligated product was digested with Psp1406I. By the digestion the Psp1406I fragment was cut out of the product having a plurality of linkers inserted therein to obtain a cosmid wherein one linker has been inserted at each of the both ends of the DNA fragment. Subsequently, the reaction solution was subjected to agarose gel electrophoresis to excise a gel containing a 2.3 kb DNA fragment. The DNA fragment was recovered from the gel by electrophoresis. Next, pAdex1cw was digested with ClaI and the resulting small fragments were removed by applying on a Spun column (Pharmacia Inc.). The remaining DNA fragment (1 μg) was reacted overnight with 0.1 μg of the aforesaid 2.3 kb DNA fragment, in total 18 μl of a solution containing ATP and T4 DNA ligase, to effect ligation. After the ligase was inactivated by incubation at 70° C. for 10 minutes, total 2 μl of ClaI was added to a ¼ amount of the reaction mixture to digest the circular cosmid resulting from self annealing, and 1 μl of the DNA fragments was used for an in vitro packaging.

The structure of the cosmid DNA prepared from each colony was confirmed by simultaneous digestion with BamHI and XhoI. Two fragments of 483 bp and 4.8 kb are formed when inserted in the intended orientation and, two fragments of 2.7 kb and 2.5 kb are formed when inserted in the inverted orientation. It was thus confirmed that the objective cassette cosmid pAdex1pCAw was obtained.

⑤ Construction of cassette cosmid 9Adex1CAwt (SAIBO KOGAKU (Cell Engineering), 13 (8), 759, 1994)

After digesting with 20 units of SwaI, ethanol precipitation was performed to recover 1 μg of pAdex1pCAw. The recovered pAdex1pCAw was mixed with 0.01 μg of a synthetic linker (2) (SEQ ID NO: 3) phosphorylated at the 5' end and containing ClaI, XbaI, SpeI, PacI, SwaI and ClaI sites as described below.

| Synthetic linker (2): |
|---|
| 5'-ATCGATTCTAGACTAGTTTAATTAATTTAAATCGAT-3'<br>3'-TAGCTAAGATCTGATCAAATTAATTAAATTTAGCTA-5' |

The mixture was reacted overnight in total 18 µl of a solution containing ATP and T4 DNA ligase to effect ligation. After the ligase was inactivated by incubation at 70° C. for 10 minutes, 20 units of PacI was added thereto for digestion. By the digestion the PacI fragment was cut out of the product having a plurality of linkers inserted therein to obtain a cosmid wherein only one linker has been inserted. Subsequently, the reaction solution was applied on a Spun column (Pharmacia Inc.) to remove small fragments derived from the linkers. Thereafter, ligation was performed overnight in total 18 µl of a solution containing ATP and T4 DNA ligase, followed by cyclization through self annealing. After the ligase was inactivated by incubation at 70° C. for 10 minutes, 1 µl of the resulting product was used for an in vitro packaging.

The structure of the cosmid DNA prepared from each colony was confirmed by simultaneous digestion with XbaI and XhoI. A 552 bp fragment is formed when inserted in the intended orientation and, a 568 bp fragment is formed when inserted in the inverted orientation. It was thus confirmed that the objective cassette cosmid pAdex1CAwt was obtained, as shown on FIG. 2.

EXAMPLE 2

Construction I of loxP-inserted cosmid

① Preparation of plasmid pA60X99X

After 0.5 µg of the cassette cosmid pAdex1CAwt was digested with 15 units of BamHI in 20 µl of a reaction solution, BamHI was inactivated by heating at 70° C. for 15 minutes. Using a ¼ amount of the reaction mixture, ligation was performed overnight in total 20 µl of a ligase buffer containing ATP and T4 DNA ligase. Using 10 µl of the reaction mixture, E. coli DH5α was transformed, and a plasmid DNA was prepared from the resulting transformant to obtain the objective plasmid pA60X99X.

② Preparation of plasmid pA60X99 (removal of XbaI site other than adenovirus)

After 5 µl of the plasmid pA60X99X was reacted for 5 minutes in 50 µl of a solution containing 10 units of XbaI, the reaction mixture was subjected to electrophoresis on an agarose gel. A gel containing a 23.8 kb DNA fragment, which was prepared by digesting only at one site of the two XbaI sites, was cut out, and the DNA fragment was recovered from the gel by electrophoresis. Next, 0.2 µg of the fragment was reacted in 50 µl of the reaction system containing 5 units of Klenow enzyme (Takara Shuzo Co., Ltd.) to fill in the both ends with the enzyme. Then, a ⅕ amount of the reaction mixture was reacted overnight in total 20 µl of a solution containing ATP and T4 DNA ligase to effect ligation. Using 10 µl of the reaction mixture, E. coli DH5α was transformed. From the thus obtained transformants, plasmid DNAs were prepared. These plasmid DNAs were simultaneously digested with BsrGI and XbaI to obtain a 6.2 kb DNA fragment, namely, plasmid pA60X99, as shown on FIG. 3.

Preparation of plasmid pA2L60X99 (insertion of loxP into the BsrGI site)

After 30 µg of plasmid pULL2r, which was prepared as described below, was digested with 150 units of XhoI in 125 µl of a reaction solution, XhoI was inactivated by heating at 70° C. for 15 minutes. Subsequently, the both ends of the DNA fragment were filled in with 12 units of Klenow enzyme (Takara Shuzo Co., Ltd.) in the reaction system. Extraction with phenol-chloroform (1:1) was followed by ethanol precipitation. The precipitates were collected by centrifugation and dissolved in 60 µl of TE buffer obtained by adding 1 mM EDTA to 10 mM Tris-hydrochloride (pH 7.5). Then, a half of the reaction mixture was reacted overnight with 0.2 µg of 5'-end-phosphorylated KpnI linker (Takara Shuzo Co., Ltd.), in total 50 µl of a ligase reaction solution containing ATP and T4 DNA ligase to effect ligation. After the ligase was inactivated by heating at 70° C. for 15 minutes, the ligation product was digested with 100 units of Asp718 in 80 µl of the reaction system. The reaction mixture was subjected to agarose gel electrophoresis. A gel containing a 64 bp DNA fragment bearing loxP was cut out, and the DNA fragment was recovered from the gel by electrophoresis.

The plasmid pULL2r used above was prepared as follows. Plasmid pUC119 (Takara Shuzo Co., Ltd.) was digested with restriction enzyme Ecl136II followed by a treatment with alkaline phosphatase. Then ligation was performed between the pUC119-Ecl136II fragment and the following synthetic DNA fragment (SEQ ID NO: 4):

| |
|---|
| 5'-CGAACGCGTATAACTTCGTATAGCATACATTATACGAAGTTATCTCGAGTCG-3'<br>3'-GCTTGCGCATATTGAAGCATATCGTATGTAATATGCTTCAATAGAGCTCAGC-5' | wherein the underlined sequence indicates the loxP site. The synthetic DNA fragment bears loxP sequence having MluI site and XhoI site at the end thereof and is designed to form NruI site when the MluI and XhoI sites are linked. Thus, plasmid pULL2r in which two of the synthetic DNA fragments have been inserted was obtained.

On the other hand, 10 µg of plasmid pA60X99 was digested with 50 units of BsrGI contained in 50 µl of a solution. Thereafter, the reaction mixture was subjected to agarose gel electrophoresis to cut out a gel containing a 23.8 kb DNA fragment. The DNA fragment was recovered from the gel by electrophoresis. The recovered DNA fragment and the aforesaid 64 bp DNA fragment bearing loxP were reacted overnight in total 25 µl of a solution containing ATP and T4 DNA ligase to effect ligation. To a half of the reaction mixture were added sterilized water and a buffer for BsrGI digestion to make the whole volume 18 µl. The mixture was incubated at 70° C. for 10 minutes to inactivate the ligase. After 20 units of BsrGI (final volume of 20 µl in total) were added to the reaction mixture, the mixture was reacted at 37° C. for an hour to digest the resulting circular pA60X99 formed by self-annealing. Using 10 µl of the reaction mixture, E. coli DH5α was transformed. From the thus obtained transformant, plasmid DNA was prepared.

In order to confirm the orientation of the loxP inserted, the plasmid DNA was simultaneously digested with ApaI and MluI, and the reaction mixture was subjected to agarose gel electrophoresis. Two fragments of 366 bp and 219 bp are formed when inserted in the intended orientation, and two fragments of 334 bp and 251 bp are formed when inserted in the inverted orientation. In the case of digestion with NruI, a 573 bp fragment is formed when inserted in the intended orientation, and a 533 bp fragment is formed when inserted in the inverted sequence. Further, in the case of concurrent digestion with DraI and KpnI, a 320 bp fragment is formed when one loxP is inserted in the intended orientation, and a 384 bp fragment is formed when two loxP sequences are inserted in the intended orientation. The objective plasmid which meets all these three conditions, namely, the objective plasmid pA2L60X99, into which only one loxP has been inserted in the intended orientation, was thus obtained as shown on FIG. 4.

④ Preparation of plasmid pA2L3L6099 (insertion of loxP into XbaI site)

After 20 μg of plasmid pULL2r was digested by reaction in 100 μl of a solution containing 100 units of XhoI, the enzyme was inactivated by heating at 70° C. for 15 minutes. Subsequently, the resulting DNA fragment was reacted in a solution containing 8 units of Klenow enzyme (Takara Shuzo Co., Ltd.) to fill in the both ends with the enzyme. Extraction of the reaction mixture with phenol-chloroform (1:1) was followed by ethanol precipitation. The precipitates were collected by centrifugation and dissolved in 30 μl of TE buffer. The whole volume of the solution was reacted overnight with 0.4 μg of 5'-end-phosphorylated SpeI linker (Takara Shuzo Co., Ltd.), in a ligase solution (final volume of 50 μl in total) containing ATP and T4 DNA ligase to effect ligation. The ligase was inactivated by incubation at 70° C. for 10 minutes. After 54 units of SpeI was further added for digestion, the reaction mixture was subjected to agarose gel electrophoresis. A gel containing a 64 bp DNA fragment of bearing loxP was cut out, and the DNA fragment was recovered from the gel by electrophoresis.

On the other hand, 10 μg of plasmid pA2L60X99 was reacted in 50 μl of a solution containing 10 units of XbaI for digestion. The reaction mixture was subjected to agarose gel electrophoresis. A gel containing a 23.8 kb DNA fragment was cut out, and the DNA fragment was recovered from the gel by electrophoresis. Then, 0.5 μg of the DNA fragment was reacted overnight with 0.005 μg of the aforesaid 64 bp DNA fragment bp bearing loxP, in total 16 μl of a ligase solution containing ATP and T4 DNA ligase to effect ligation. To the reaction mixture was added 14 μl of 5-fold-diluted TE, and the ligase was inactivated by incubation at 70° C. for 10 minutes. Thereafter, total 20 μl of 20 units of XbaI was added to a ¼ volume of the reaction mixture to digest the resulting circular pA2L60X99 formed by self-annealing. Using 10 μl of the reaction mixture, E. coli DH5α was transformed. From the thus obtained transformant, plasmid DNA was prepared.

In order to confirm the orientation of the loxP inserted, the plasmid DNA was simultaneously digested with BglII and MluI, and the reaction mixture was subjected to agarose gel electrophoresis. Two fragments of 366 bp and 503 bp are formed when inserted in the intended orientation and, two fragments of 398 bp and 471 bp are formed when inserted in the inverted orientation. In the case of simultaneous digestion with ApaI and MluI, a 660 bp fragment is formed when inserted in the intended orientation and, a 628 bp fragment is formed when inserted in the inverted orientation. Further, in the case of concurrent digestion with EcoNI and MluI, a 311 bp fragment is formed when inserted in the intended orientation and, a 343 bp fragment is formed when inserted in the inverted orientation. Further, in the case of concurrent digestion with HpaI and SacI, a 397 bp fragment is formed when one loxP is inserted in the intended orientation and, a 461 bp fragment is formed when two loxP sequences are inserted in the intended orientation. The objective plasmid which meets all these four conditions, namely, the objective plasmid pA2L3L6099, into which only one loxP has been inserted in the intended orientation, was thus obtained as shown on FIG. 5.

⑤ Construction of cassette cosmid pAdex2L3LCAwt

After 10 μg of cassette cosmid pAdex1CAwt was digested in 100 μl of a reaction solution containing 40 units of Csp45I, 30 units of BamHI and 40 units of EcoRI were successively added to the reaction solution. Agarose gel electrophoresis is performed for inspection. A gel containing a 21 kb DNA fragment was cut out, and from the gel the DNA fragment was recovered by electrophoresis. When the 21 kb BamHI-DNA fragment was recovered, digestion with Csp45I and EcoRI was made to prevent contamination with other fragments.

After 5 μg of the plasmid pA2L3L6099 was digested in 50 μl of a solution containing 30 units of BamHI, the DNA fragments were extracted with phenol-chloroform (1:1). The aqueous layer was subjected to gel filtration using Sephadex G25, previously equilibrated with TE. Then, 0.5 μg of the recovered DNA fragment was ligated with 0.5 μg of the aforesaid 21 kb DNA fragment overnight in total 18 μl of a solution containing ATP and T4 DNA ligase. After the ligase was inactivated by incubation at 70° C. for 10 minutes, 1 μl of the cassette cosmid was used for an in vitro packaging.

That is, a lambda in vitro packaging kit, Gigapack XL (Stratagene Co., Ltd., USA) was used in a ¼ scale, and the remaining solution was lyophilized at −80° C. Since Gigapack XL provides a low package efficiency for a 42 kb or less cosmid, the kit can select at a certain extent a cosmid having become a larger size by including an insert sequence. In this experiment, when 10 colonies were picked up, most of them included the insert sequence. Therefore, the clone having the desired orientation (i.e., the clone in which viral genome is correctly ligated) could be readily obtained. The cosmid was treated in a conventional manner described in Izumu Saito, et al., JIKKEN IGAKU (Experimental Medicine), 7, 183–187 (1989).

The packaged cosmid was transfected into E. coli DH5α (GIBCO BRL). That is, the cosmid was inoculated on each of three Ap+ agar plates (supplemented with ampicillin) and 5 ml of Ap+ LB (pool) in amounts of ½₀₀, ½₀, ½ and the balance, respectively, followed by incubation overnight.

The miniprep DNA from the pool was then extracted and prepared to examine a ratio of the cosmid having the insert sequence by digestion with restriction enzyme DraI. The colony was picked up together with the agar plate, and cultured in Ap+ LB overnight to prepare the miniprep DNA.

Next, the structure of the cosmid prepared from each colony was confirmed by digestion with DraI. When inserted in the intended orientation, a 891 bp fragment is formed and, when inserted in the inverted orientation, a 1.4 kb fragment is formed. It was thus confirmed that the objective cassette cosmid pAdex2L3LCAwt was obtained.

EXAMPLE 3

Preparation of adenoviral DNA-terminal protein complex (Ad5 d1X DNA-TPC and Adex1CANLacZ DNA-TPC)

① As an adenovirus DNA, Ad5 d1X (I. Saito et al., J. Virology, vol. 54, 711–719 (1985)) or Adex1CANLacZ was used. Ad5 d1X DNA and Adex1CANLacZ were transfected into HeLa cells at the amount of 10 Roux tubes and 293 cells, respectively, and then incubated.

That is, the viral solution (~10⁹ PFU/ml) of Ad5-d1X or Adex1CANLacZ was transfected at the amount of 0.2 ml/Roux tube. Three days after, the cells peeled off were collected by centrifugation. Most of the adenovirus particles existed in the nucleus, not in the medium. The virus is therefore advantageously purified from the infected cells.

The following procedures were aseptically performed.

② The thus obtained cells were suspended in Tris-HCl (pH 8.0) and sonicated using a sealed type sonicator to destroy the cells thereby to release the virus.

③ After the thus obtained cell debris was removed by centrifugation, the supernatant was overlaid on cesium chloride solution (specific gravity of 1.43) charged in a ultracentrifuging machine SW28 tube, followed by concentration through cushion centrifugation.

④ The virus layer immediately below the interface was transferred to a SW 50.1 tube. In general, the virus layer immediately below the interface was visually observed, and 5 ml of the virus layer was collected. At the same time, another tube was filled up with the cesium chloride solution (specific gravity of 1.34).

These tubes were centrifuged at 4° C. overnight at 35 k rpm. Then, the thus formed white layer indicating virus existence was collected, and transferred onto a tube which previously formed gradients. The tube was further ultracentrifuged at 4° C. for 4 hours at 35 k rpm.

⑤ The white layer indicating virus existence was collected, and mixed with an equal volume of 8M guanidine hydrochloride. Furthermore, 4M guanidine hydrochloride-saturated cesium chloride was added to the mixture. The resulting mixture was filled in a VTi65 tube. The protein particle was denatured with 4M guanidine hydrochloride to cause dissociation, whereby the DNA-TPC complex was released.

⑥ The tube described above was subjected to ultracentrifugation at 15° C. overnight at 55 k rpm, followed by fractionation with 0.2 ml. From the fractions, 1 μl each was packed up, and mixed with 1 μg/ml of ethidium bromide aqueous solution to confirm the presence or absence of a DNA with fluorescence-staining. Two or three fractions containing DNA were collected.

⑦ The fractions were dialyzed twice against 500 ml of TE overnight, and then stored at −80° C. The amount of the thus obtained Ad5d1X DNA-TPC complex or Adex1CANLacZ DNA-TPC complex was determined on the basis of OD₂₆₀ value in a conventional method for determining DNA.

⑧ The resulting Ad5d1X DNA-TPC complex or Adex1CANLacZ DNA-TPC complex was digested with AgeI at a sufficient amount for 2 hours. After gel filtration through Sephadex G25 column, the complex was stored at −80° C.

In the meantime, the DNA-TPC complex might undergo digestion with restriction enzymes, dialysis and gel filtration, but might not undergo electrophoresis, phenol treatment and ethanol precipitation. The cesium chloride equilibrium centrifugation only is available as a concentration method. Therefore, the DNA-TPC complex system was maintained at a concentration as high as possible. Approximately 300 μg of the DNA-TPC complex could be obtained from the infected cells of 10 Roux tubes.

⑨ An aliquot of the DNA-TPC complex solution was collected, and 10 μl of BPB buffer for electrophoresis was added thereto. Then, 1 μl of proteinase K (10 mg/ml) was added to the mixture. The resulting mixture was incubated at 37° C. for 10 minutes to digest the terminal protein in the DNA-TPC complex. After phenol extraction, the supernatant was separated by electrophoresis on an agarose gel to confirm completion of the digestion.

After the restriction enzyme buffer in the EcoT221-digested DNA-TPC was removed by centrifugational gel filtration, the resulting products were separately charged in tubes and stored at −80° C.

EXAMPLE 4

Preparation of loxP-inserted recombinant adenoviruses (Ad5d1X2L3L and Adex2L3LCANLacZ)

NLacZ gene is obtained by adding the nuclear transfer signal sequence of SV40 to 5'-end of LacZ gene of *E. coli*.

① Each one of 6 cm and 10 cm diameter Petri dishes was charged with the 293 cells cultured in DME supplemented with 10% FCS.

② After 8 μg of the loxP-inserted cosmid pAdex2L3LCAwt DNA having the expression unit introduced therein was mixed with 1 μg of Ad5d1X DNA-TPC complex previously digested with AgeI or mixed with 1 μg of Adex1CANLacZ DNA-TPC complex previously digested with AgeI, transfection was effected on the 6 cm Petri dish using Celfect Kit (Pharmacia) according to a calcium phosphate method. That is, the mixture was dropped onto the medium in the 6 cm Petri dish, and the incubation was continued.

After incubation overnight (for about 16 hours), the culture medium was exchanged in the next morning. Then, in the evening, the medium containing cells was poured with 5% FCS-containing DME into wells in three 96-well collagen coated plates (non-diluted stock solution, 10-fold diluted, and 100-fold diluted solution) at the amount of 0.1 ml/well. In order to avoid a significant difference in the cell count between each plate, one third of the 293 cells harvested from 10 cm Petri dish were added on each of two diluted solution plates.

③ Three or four days after and eight to ten days after, 50 μl of 10% FCS-containing DME was further added to each well. When the 293 cell lines became thin, 10% FCS-containing DME was earlier added to the well.

The wells, wherein the virus propagated and the cells were dead, were observed in 7 to 20 days. From every wells wherein the cells were completely dead, the culture media containing dead cells was transferred with a sterile pasteur pipette into a 1.5 ml sterilized tube. The tube was quickly lyophilized and stored at −80° C.

④ The observation was finished in 15 to 25 days. About ten (10) tubes were selected from the tubes charged with the culture media containing the cells which were dead at a relatively late stage. After ultrasonication, centrifugation was conducted at 5 k rpm for 10 minutes. The resulting supernatant was stored at −80° C. for use as a first seed.

The wells in which the virus started to propagate at an earlier stage suggest a higher probability of mixed infections with a plurality of virus strains.

⑤ The 293 cell lines were charged in a 24-well plate, and 5% FCS-DME (0.4 ml/well) and 10 μl of the first viral seed were added to wells in duplicate.

⑥ Where the cells were completely dead in about 3 days, the supernatant was obtained from one of the duplicate wells by ultrasonication and centrifugation in a manner similar to the procedures for preparing the first viral seed as described above. The thus obtained supernatant was stored at −80° C. for use as a second seed. The dead cells in another well of the duplicate wells were centrifuged at 5000 rpm for 5 minutes, and the supernatant was discarded. The cells alone were stored at −80° C. (cell pack). The cell packs of 10 viral strains were collected, and the entire DNA was extracted from the infected cells according to the following procedures. To each cell pack were added 400 µl of TNE for cell DNA (50 mM Tris-HCl, pH 7.5, 100 mM NaCl, 10 mM EDTA), 4 µl of proteinase K (10 mg/ml) and 4 µl of 10% SDS.

⑦ After treating at 50° C. for an hour, extraction was performed twice with phenol-chloroform and twice with chloroform, and then ethanol precipitation was performed. The nucleic acid recovered by ethanol precipitation was dissolved in 50 µl of TE containing 20 µg/ml ribonuclease.

After 15 µl of the solution was digested with XhoI recognizing a site contains CG, the digested product was subjected, together with the XhoI-digested product of the expression cosmid cassette, to electrophoresis overnight on agarose gel having a length of about 15 cm. The patterns thus obtained were compared. Selected was the clone which showed a band indicating the digestion pattern of two loxP sequences inserted therein. The clones which provided many bands indicating undetermined DNA sequences were discarded, since there is a possibility that the clones would be contaminated with the virus having deletions.

EXAMPLE 5

Construction of E2A gene-deleted adenovirus and confirmation of its structure

Recombinant adenoviruses Adex2L3LCANLacZ and Adex1CANCre were transfected into 293 cells at moi of 10, followed by incubation. NCre gene was obtained by adding a nuclear transfer signal sequence of SV40 to 5'-end of Cre gene.

Four days after, DNA was prepared by the procedures described hereinabove. It was confirmed by the two methods, i.e., digestion with SmaI and PCR as described in detail below, that the formed Adexd123CANLacZ has such a structure that the E2A gene-containing region located between the two loxP sequences has been cut out.

1. Digestion with SmaI

After digestion with SmaI, gel electrophoresis was performed. As the result, it was noted that the region located between the two loxP sequences was cut out and hence, a 4.7 kb fragment was formed. From comparison in band density between the above 4.7 kb band and the band of 4.45 kb commonly observed in Adex2L3LCANLacZ, Adex1CANCre and Adexd123CANLacZ, it was determined that about 30% segment in the recovered recombinant adenovirus was Adexd123CANLacZ.

2. Confirmation by PCR

PCR reaction was conducted under conventional conditions, using 0.1 ng of the prepared DNA as a template. The product was analyzed by electrophoresis on an agarose gel. Primers employed are preferably Oligonucleotide (1) (SEQ ID NO: 5), Oligonucleotide (2) (SEQ ID NO: 6), Oligonucleotide (3) (SEQ ID NO: 7) and Oligonucleotide (4) (SEQ ID NO: 8), as shown below.

| Oligonucleotide (1) |
| --- |
| 5'-CAACTCCATGCTCAACAGTCCCCAGGTACA-3' |
| Oligonucleotide (2) |
| 5'-GATTTTTAAACGGCGCAGACGGCAAG-3' |
| Oligonucleotide (3) |
| 5'-GTGAGCTTAGAAAACCCTTAG-3' |
| Oligonucleotide (4) |
| 5'-AGATACCCCTTTTGCACTGGTGCAAGTTAAC-3' |

Composition of reaction solution for PCR (20 µl in total volume):

| | |
| --- | --- |
| Tris-HCl (pH 8.3) | 10 mM |
| KCl | 50 mM |
| MgCl$_2$ | 1.5 mM |
| dNTP mixture | 0.2 mM |
| primer | 0.2 µM each |
| template DNA | 0.1 ng |
| Taq polymerase | 0.5 units |

Reaction conditions for PCR:

| | |
| --- | --- |
| Temperature for dissociating double strand: | 95° C., 1.5 minutes |
| Temperature for annealing: | 64° C., 1.0 minute |
| Temperature for chain extension reaction: | 70° C., 1.0 minute |
| Reaction cycle: | 30 times |

The results are shown in FIG. 6.

Where Oligonucleotides (1) and (4) were employed as primers, a band which is assumed to show a bp sequence was detected, indicating that Adexd123CANLacZ deleted of E2A gene was present, as shown at Lane 1 in FIG. 6.

Where Oligonucleotides (2) and (3) were used as primers, a band which is assumed to show a 221 bp sequence was detected, supporting the presence of circular E2A gene cut out by the Cre gene product, as shown at Lane 2 in FIG. 6.

From the results of 1 and 2 above, it is thus revealed that Adexd123CANLacZ in which the E2A gene region located between the loxP sequences has been excised from Adex2L3LCANLacZ was formed.

REFERENCE EXAMPLE 1

Construction of recombinant adenoviral vector bearing recombinase Cre gene and CAG promoter (1) Construction of cassette cosmid for expressing recombinase Cre gene ① A PCR reaction was conducted using *E. coli* phage P1 DNA containing recombinase Cre gene (ATCC 11303-B23) as a template, the following oligonucleotide (SEQ ID NO: 9) as a 5'-primer, the following oligonucleotide (SEQ ID NO: 10) as a 3'-primer, and Vent$^R$(made by NEB) as a thermostable polymerase. The PCR reaction was conducted under the conditions given below. The product was subjected to electrophoresis on an agarose gel, and a band indicating about 1 kb was excised from the agarose gel to obtain an about 1 kb DNA fragment bearing recombinase Cre gene.

5'-Primer

5'-CGT CTGCAG TGCA TCATGA GTAATTTACTGACCGTACACCAAAATTTGCCTGC-3'
    PstI        BspHI

3'-Primer

3'-GACCTTCTACCGCTAATCGGTAAT TCGCGAGATCT CGG-5'
                            Aor51HI; XbaI

The underlined portions denote the recognition sites of restriction enzymes.

| Conditions for PCR | |
|---|---|
| Buffer: 10 mM KCl, 20 mM Tris-HCl (pH 8.8), 10 mM $(NH_4)_2SO_4$, 2 mM $MgSO_4$, 0.1% Triton X-100 (buffer offered from NEB was used) | |
| Polymerase: | 2 units |
| dNTP: | 400 µM |
| Primer: | 1 µM |
| P1 phage DNA: | 1 ng |
| Temperature for dissociating double strand: | 95° C., 1.5 minutes |
| Temperature for annealing: | 60° C., 1.5 minutes |
| Temperature for chain extension reaction: | 74° C., 2.0 minutes |
| Reaction cycle: | 20 times |

After each of the thus obtained DNA fragment and pUC19 (Takara Shuzo Co., Ltd., Japan) was digested with restriction enzymes PstI (Takara Shuzo Co., Ltd.) and XbaI (Takara Shuzo Co., Ltd. ), the digested products were recovered, and the products from the DNA fragment were mixed with the product from pUC19 in a molar ratio of approximately 3:1. The mixture was then ligated using T4 DNA ligase (Takara Shuzo Co., Ltd.). The reaction mixture was used to transform *E. coli* JM109 strain (ATCC 53323). The treated *E. coli* cells were inoculated on LB agar plate supplemented with 100 µg/ml ampicillin, and the transformants growing on the agar were selected to obtain a plasmid pUCCre bearing recombinase Cre gene.

Subsequently, the cassette cosmid pAdex1CAwt containing CAG promoter was digested with SwaI. Then, 1 µg of the digested product was mixed with 0.1 µg of about 1 Kb DNA fragment obtained by digesting the plasmid pUCCre with PstI and XbaI and blunting with Klenow enzyme (Takara Shuzo Co., Ltd.).

② Ethanol was added to the mixture obtained above to precipitate the cosmid. The precipitates were recovered by centrifugation, and dissolved in a 5-fold diluted TE solution (10 mM Tris-HCl (pH 7.5), supplemented with 1 mM EDTA).

③ The resulting solution containing the cosmid was subjected to a ligation reaction overnight in a final volume of 7 µl, with ATP and T4 DNA ligase in a buffer solution. Sterilized water and a buffer solution for Swa1 reaction were added thereto to make the whole volume 48 µl. Then, the ligase was inactivated with heating at 70° C. for 10 minutes.

Unlike a plasmid, a cosmid may usually efficiently package macromolecular DNA which has been formed by linking with each other in a linear tandem form instead of a cyclic form.

④ After adding 2 µl of SwaI (Boehringer), digestion of the cosmid was carried out at 25° C. for an hour. The reasons why the cosmid was digested with Swa1 are given below.

If a cassette cosmid is religated without the inclusion of an expression unit therein, a SwaI recognition site will be regenerated. Thus, the digestion with SwaI can recleave the cosmid having no expression unit included therein, resulting in that no colony is formed. This is a potential method for selecting only a cassette cosmid having an insert sequence therein.

⑤ The cassette cosmid was subjected to phenol extraction, centrifugation and gel filtration according to a conventional method as described in Molecular Cloning, vol. 3, E.34.

⑥ The digestion with SwaI was carried out again. That is, 5 µl of Swa1 was added to the buffer for the SwaI reaction to digest the cosmid at 25° C. for 2 hours. The digestion was conducted for the reasons as explained above.

⑦ The resulting cosmid (1 µl ) was subjected to an in vitro packaging.

That is, a lambda in vitro packaging kit, Gigapack XL (Stratagene Co., Ltd.) was used in a ¼ scale, and the remaining solution was lyophilized at −80° C. Since Gigapack XL provides a low package efficiency for a 42 kb or less cosmid, the kit can select at a certain extent a cosmid having become a larger size by including an insert sequence. In this experiment, when 10 colonies were picked up, most of them included the insert sequence. Therefore, the clone having the intended orientation (i.e., the orientation toward the left side which means the orientation from E3 gene region to E1 gene region) could be readily obtained.

The cosmid was manipulated according to a conventional method as described in Izumu Saito et al., JIKKEN IGAKU (Experimental Medicine), vol. 7, 183–187, 1989.

⑧ The packaged cosmid was transfected into *E. coli* strain DH1 (ATCC 33849).

That is, the cosmid was inoculated on each of three $Ap^+$ agar plates (supplemented with ampicillin) and 5 ml of $Ap^+$ LB (pool) in amount of each of 1/200, 1/20, ½ and the balance, respectively, and then incubation was performed overnight.

The miniprep DNA from the pool was extracted and prepared. A ratio of the cosmid having the insert sequence was examined according to whole enzymatic digestion. The colony was picked up together with the agar plate, and cultured in 1.5 ml of $Ap^+$ LB overnight to prepare the miniprep DNA.

⑨ The orientation and structure of the expression unit included in the cosmid were confirmed by digestion with restriction enzymes.

A plasmid bearing the expression unit but deleted of most adenovirus DNA was prepared using NruI and a ligase. A DNA fragment was then prepared from the plasmid for final confirmation of cDNA cloning.

(2) Preparation of adenoviral DNA-protein complex (Ad5 d1X DNA-TPC)

① As an adenovirus DNA, a vector Ad5 d1X (I. Saito et al., J. Virology, vol. 54, 711–719 (1985)) was used. The vector Ad5 d1X DNA was infected into HeLa cells at the amount of 10 Roux tubes, followed by incubation.

That is, the viral solution (~$10^9$ PFU/ml) of Ad5-d1X was infected at the amount of 0.2 ml/Roux tube. Three days after, the cells peeled off were collected with centrifugation at 1500 rpm for 5 minutes. Most of the adenovirus particles existed in the nucleus, not in the medium. Therefore, the virus was advantageously purified from the infected cells.

The following procedures were aseptically performed.

② The thus obtained cells were suspended in 20 ml of 10 mM Tris-HCl (pH 8.0) and sonicated at 200 W for 2 minutes (30 seconds×4) using a sealed type sonicator to destroy the cells thereby to release the virus.

In order to release the virus from the cells, when the cell suspension has the volume of 5 ml or less, five repetitions of freeze-thawing are sufficient. However, when having a larger volume, a sonicator is advantageous for releasing the virus. In this case, a sealed type sonicator with an exclusive cup must be used. An ordinary throw-in type is dangerous, even if the operation is performed in a safety cabinet.

③ After the thus obtained cell debris were removed by centrifugation at 10 k rpm for 10 minutes, the supernatant was overlaid on 15 ml of cesium chloride solution (specific gravity of 1.43) charged in a ultracentrifuging machine (SW28 tube), followed with concentration by centrifugation (25 k rpm, an hour, 4° C.).

④ The virus layer immediately below the interface was transferred to a SW 50.1 tube. The virus layer immediately below the interface was visually observed, and 5 ml of the virus band was collected. At the same time, another tube was filled up with the cesium chloride solution (specific gravity of 1.34).

These tubes were centrifuged at 4° C. overnight at 35 k rpm. Then, the thus formed layer indicating virus existence was collected, and transferred onto a tube which previously formed gradients. The tube was further subjected to ultracentrifugation at 4° C. for 4 hours at 35 k rpm.

⑤ The white layer indicating virus existence was collected, and mixed with an equal volume of 8M guanidine hydrochloride. Furthermore, 4M guanidine hydrochloride-saturated cesium chloride was added to the mixture. The resulting mixture was filled in a VTi65 tube. The protein particle was denatured with 4M guanidine hydrochloride to cause dissociation, whereby the DNA-TPC complex was released. Ethidium bromide could not be used in this experiment, because any procedure for removing the ethidium bromide used has not yet been established.

⑥ The tube described above was subjected to ultracentrifugation at 15° C. overnight at 55 k rpm, followed by fractionation with 0.2 ml. From each of the fractions, 1 µl was packed up, and mixed with 1 µg/ml of ethidium bromide aqueous solution to confirm the presence or absence of a DNA with fluorescence-staining. Two or three fractions containing a DNA were collected.

⑦ The fractions were twice dialyzed against 500 ml of TE overnight, and then stored at −80° C. The amount of the thus obtained Ad5d1X DNA-TPC complex was determined on the basis of $OD_{260}$ value in a conventional method for determining DNA.

⑧ The resulting Ad5d1X DNA-TPC complex was digested with EcoT22I at a sufficient amount for 2 hours, and then stored at −80° C.

In the meantime, the DNA-TPC complex might undergo digestion with restriction enzymes, dialysis and gel filtration, but might not undergo electrophoresis, phenol treatment and ethanol precipitation. The cesium chloride equilibrium centrifugation only is available as a concentration method. Therefore, the DNA-TPC complex system was maintained at a concentration as high as possible. Approximately 300 µg of the DNA-TPC complex could be obtained from the infected cells of 10 Roux tubes.

⑨ An aliquot of the DNA-TPC complex solution was collected, and 10 µl of BPB buffer for electrophoresis was added thereto. Then, 1 µl of proteinase K (10 mg/ml) was added to the mixture. The resulting mixture was incubated at 37° C. for 10 minutes to digest the terminal protein in the DNA-TPC complex. After phenol extraction, the supernatant was separated by electrophoresis on an agarose gel to confirm the completion digestion.

After the restriction enzyme buffer in the EcoT22I-digested DNA-TPC was removed by centrifugational gel filtration, the resulting products were separately charged in tubes and stored at −80° C.

(3) Isolation of recombinant virus and preparation of high titer viral solution

① Each one of 6 cm and 10 cm diameter Petri dishes was charged with the 293 cell lines cultured in DME supplemented with 10% FCS.

② After 8 µg (3 µg to 9 µg is appropriate) of pAdex1W DNA having the expression unit introduced therein was mixed with 1 µg of Ad5d1X DNA-TPC complex previously digested with EcoT22I, the resulting mixture was transfected into the 293 cell lines on the 6 cm Petri dish using Celfect Kit (Pharmacia) according to a conventional calcium phosphate method. That is, the mixture was dropped onto the medium in the 6 cm Petri dish, and the incubation was continued.

After the overnight incubation (for about 16 hours), the culture medium was exchanged in the next morning. Then, in the evening, the medium containing cells was poured with 5% FCS-containing DME into wells in three 96-well collagen coated plates (non-diluted, 10-fold diluted, and 100-fold diluted solutions). In order to avoid a significant difference in the cell count between each plate, one third of the 293 cells harvested from 10 cm Petri dish were added on each of two diluted solution plates.

③ Three or four days after and eight to ten days after, 50 µl of 10% FCS-containing DME was further added to each well. When the 293 cell lines became thin, 10% FCS-containing DME was earlier added to the well.

The wells, wherein the virus propagated and the cells were dead, were observed in 7 to 15 days. From every wells wherein the cells were completely dead, the culture media containing dead cells was transferred with a sterile pasteur pipette into a 1.5 ml sterilized tube. The tube was quickly frozen and stored at −80° C.

④ The observation was finished in 15 to 18 days. About ten (10) tubes were selected from the tubes charged with the culture media containing the cells which were dead at a relatively late stage. After six (6) repetitions of the freeze-thawing, centrifugation was conducted at 5 k rpm for 10 minutes. The resulting supernatant was stored as a first seed at −80° C.

The wells in which the virus started to propagate at an earlier stage suggest a higher probability of mixed infections with a plurality of virus strains.

⑤ The 293 cell lines were charged in a 24-well plate, and 5% FCS-DME (0.4 ml/well) and 10 µl of the first viral seed were added to wells in duplicate.

⑥ Where the cells were completely dead in about 3 days, the supernatant was obtained from one of the duplicate wells by six (6) repetitions of freeze-thawing and centrifugation in a manner similar to the procedures for preparing the first viral seed as described above. The thus obtained supernatant was stored at −80° C. for use as a second seed. The titer of the second viral solution was approximately $10^7$ to $10^8$ PFU/ml. The dead cells in another well of the duplicate wells were centrifuged at 5 k rpm for 5 minutes, and the supernatant was discarded. The cells alone were stored at −80° C. (cell pack). The cell packs of 10 viral strains were collected, and the entire DNA was extracted from the infected cells according to the following procedures. To each cell pack were added 400 µl of TNE (50 mM Tris-HCl, pH 7.5, 100 mM NaCl, 10 mM EDTA), 4 µl of proteinase K (10 mg/ml) and 4 µl of 10% SDS.

⑦ After treating at 50° C. for an hour, extraction twice with phenol-chloroform, extraction twice with chloroform and then ethanol precipitation were performed. The nucleic acid recovered by ethanol preparation was dissolved in 50 µl of TE containing 20 µg/ml ribonuclease.

After 15 µl of the solution was digested with XhoI recognizing a site contains CG, the digested product was subjected, together with the XhoI-digested product of an expression cosmid cassette, to electrophoresis overnight on agarose gel having a length of about 15 cm. The patterns thus obtained were compared. Selected were the clone which showed a band indicating accurately the DNA sequence from the cleaved site in the expression unit to the left end of the adenovirus genome. The clones which provided many bands indicating undetermined DNA sequences were discarded, since there was a possibility that the clones would be contaminated with the virus having deletions.

An adenovirus DNA generally propagates at a level of 10,000 copies/cell. Accordingly, a whole DNA including a native cellular DNA and adenoviral DNA could be extracted, digested with restriction enzymes and then subjected to electrophoresis, thereby to observe bands indicating DNA fragments derived from the adenoviral DNA. The restriction enzyme such as XhoI specific for a site containing CG hardly digests the cellular DNA. As the result, when loaded on electrophoresis, the patterns could be readily observable and distinguishable. When using other enzymes, the non-infected 293 cell line DNA was required as a control. In this case, a band derived from a repeated sequence of human cell.

⑧ The second seed solution, which was confirmed by the XhoI digestion, was transfected at an amount of 0.1 ml into the 293 cell lines charged in a 150 cm² collagen-coated bottle containing 25 ml of medium.

When the cells were dead in three days, the culture medium containing dead cells was treated aseptically with a sealed type sonicator at the maximum output of 200 w for 2 minutes (30 seconds×4) to release the virus.

The precipitates were removed by centrifugation at 3 k rpm for 10 minutes at 4° C., and the obtained supernatant was charged at an amount of 2 ml in each of 13 tubes of 5 ml freezing tube. The tubes were quickly frozen with dry ice and stored at −80° C. to prepare a third seed solution. The third seed solution which contains the recombinant adenoviral vector of the present invention showed a titer as high as $10^9$ PFU/ml.

After transfecting 5 µl of the third seed solution into one well containing the 293 cell lines in a 24-well plate, the propagated viral DNA was digested with restriction enzymes and then subjected to electrophoresis. The resulting patterns were confirmed by the procedures as described hereinabove. Where there was any doubt that the virus would be possibly mixed with the deleted virus or the parent virus, all of the third seeds were discarded. This is because there would be a possibility that the deleted virus, which had already existed in the second viral solution, rapidly propagated at an appreciable level. Therefore, the above procedures were again performed with another second seed solution. Alternatively, the virus solution was purified by subjecting the first seed solutions according to a limiting dilution method.

According to the present invention, there are provided recombinant DNA viruses by which a foreign gene may be transduced into a variety of animal cells in a stable form. The present invention also provides a simple process for producing the recombinant DNA viruses. Particularly, the recombinant adenoviruses of the present invention are useful for the treatment of hereditary diseases.

The complete disclosure of Japanese Patent Application Nos. 7-84891 and 7-276335 is incorporated herein by reference.

---

What is claimed is:

1. A recombinant adenovirus comprising an adenovirus genome having a foreign gene and a promoter for expressing said foreign gene, wherein the function of an E2A gene is completely deleted by removing a part or all of said E2A gene.

2. The recombinant adenovirus of claim 1, wherein said foreign gene and said promoter for expressing said foreign gene are inserted in an orientation opposite to the natural transcription orientation of E1A and E1B genes.

3. The recombinant adenovirus of claim 1, wherein said adenovirus genome has a deletion of an E1A gene.

4. The recombinant adenovirus of claim 1 or 8 wherein said foreign gene and said promoter for expressing said foreign gene are inserted in a deletion.

5. The recombinant adenovirus or claim 4, wherein said adenovirus genome has an E3 gene region deletion of genome map units 79.6 to 84.8%.

6. The recombinant adenovirus of claim 1, wherein said promoter for expressing said foreign gene is a hybrid CAG promoter comprising a cytomegalovirus enhancer, a chicken β-actin promoter, a rabbit β-globin splice acceptor and a poly(A) sequence.

7. A recombinant adenovirus comprising an adenovirus genome having two recombinase-recognition sequences in the same orientation located on both sides of an E2A gene.

8. The recombinant adenovirus of claim 7, wherein one of said two recombinase-recognition sequences is located between the termination codons of an E2A gene and an L3 gene, without preventing proliferation of said recombinant adenovirus.

9. The recombinant adenovirus of claim 8, wherein the other of said two recombinase-recognition sequences is located in the segment from 79.6 to 84.8% genome map units of said adenovirus genome.

10. The recombinant adenovirus of claim 7, wherein said recombinase is a Cre recombinase derived from *Eschericha coli* P1 phage.

11. The recombinant adenovirus of claim 7, wherein each of said recombinase-recognition sequences is representing by SEQ ID NO:1 of loxP which is a substrate for Cre recombinase.

12. The recombinant adenovirus of claim 7, further comprising a foreign gene.

13. The recombinant adenovirus of claim 12, further comprising a promoter for expressing said foreign gene.

14. The recombinant adenovirus of claim 13, wherein said foreign gene and said promoter for expressing said foreign gene are inserted in an orientation opposite to the natural transcription orientation of E1A and E1B genes.

15. The recombinant adenovirus of claim 7, wherein said adenovirus genome has a deletion of an E1A gene.

16. The recombinant adenovirus of claim 15, wherein said foreign gene and said promoter for expressing said foreign gene are inserted in a deletion.

17. The recombinant adenovirus or claim 16, wherein said adenovirus genome has an E3 gene region deletion of genome map units 79.6 to 84.8%.

18. The recombinant adenovirus of claim 13, wherein said promoter for expressing said foreign gene is a hybrid CAG promoter comprising a cytomegalovirus enhancer, a chicken β-actin promoter, a rabbit β-globin splice acceptor and a poly(A) sequence.

19. A method for constructing a recombinant adenovirus without a functional E2A gene, which comprises the steps of:

transducing an animal cell line with an adenovirus vector
(a) having inserted therein a promoter, a recombinase gene and a poly(A) sequence, and a recombinant adenovirus (b) comprising an adenovirus genome having two recombinase-recognition sequences located in the same orientation on both sides of an E2A gene region and excising the E2A gene region located between said two recombinase-recognition sequences.

20. The method for constructing a recombinant adenovirus of claim 19, wherein one of said two recombinase-recognition sequences is located between the termination codons of an E2A gene and an L3 gene, without preventing proliferation of said recombinant adenovirus(b).

21. The method for constructing a recombinant adenovirus of claim 19, wherein said recombinase is a Cre recombinase derived from *Escherichia coli* P1 phage.

22. The method for constructing a recombinant adenovirus of claim 19, wherein each said recombinase-recognition sequences is represented by SEQ ID NO:1 of loxP which is a substrate for a Cre recombinase.

23. The method for constructing a recombinant adenovirus of claim 19, wherein said recombinant adenovirus (b) further comprises a foreign gene.

24. The method for constructing a recombinant adenovirus of claim 19, wherein said recombinant adenovirus (b) further comprises a promoter for regulating expressing said foreign gene.

25. The recombinant adenovirus of claim 24, wherein said foreign gene and said promoter for expressing said foreign gene are inserted in an orientation opposite to the natural transcription orientation of E 1A and E 1 B genes.

26. The method for constructing a recombinant adenovirus of claim 19, wherein each of said adenovirus vector (a) and said recombinant adenovirus (b) has a deletion of an E1A gene.

27. The method for constructing a recombinant adenovirus of claim 26, wherein said foreign gene and said promoter for expressing said foreign gene of said recombinant adenovirus (b) are inserted in a deletion.

28. The method for constructing a recombinant adenovirus of claim 27, wherein said adenovirus genome of said recombinant adenovirus (b) has an E3 gene region deletion of genome map units 79.6 to 84.8%.

29. The method for constructing a recombinant adenovirus of claim 24, wherein said promoter for expressing said foreign gene is a hybrid CAG promoter comprising a cytomegalovirus enhancer, a chicken β-actin promoter, a rabbit β-globin splice acceptor and a poly(A) sequence.

30. The method for constructing a recombinant adenovirus of claim 19, wherein the function of E1A genes in said adenovirus vector (a) and said recombinant adenovirus (b) is deleted, and said animal cell line expresses an E1A gene.

31. A recombinant adenovirus comprising an adenovirus genome having a foreign gene inserted between the termination codons of an E2A gene and an L3 gene.

* * * * *